United States Patent
Ehrenreich

(10) Patent No.: US 8,168,589 B2
(45) Date of Patent: May 1, 2012

(54) USE OF ERYTHROPOIETIN AND SUBSTANCES INCREASING AND/OR PROLONGING THE ACTIVATION AND/OR STIMULATION OF ERYTHROPOIETIN RECEPTORS FOR TREATING AND/OR PREVENTING SCHIZOPHRENIA AND RELATED PSYCHOSES

(76) Inventor: Hannelore Ehrenreich, Gottingen (DE)

( * ) Notice: Subject to any disclaimer, the term of this patent is extended or adjusted under 35 U.S.C. 154(b) by 220 days.

(21) Appl. No.: 11/895,398

(22) Filed: Aug. 24, 2007

(65) Prior Publication Data

US 2009/0036359 A1    Feb. 5, 2009

Related U.S. Application Data

(63) Continuation-in-part of application No. 10/363,617, filed on Jun. 17, 2003, now abandoned.

(30) Foreign Application Priority Data

Sep. 4, 2000   (DE) .................................. 100 43 457

(51) Int. Cl.
*A61K 38/18* (2006.01)
*A61P 25/18* (2006.01)
*C07K 14/505* (2006.01)

(52) U.S. Cl. ........................ 514/7.7; 514/17.5; 530/397

(58) Field of Classification Search ........................ None
See application file for complete search history.

(56) References Cited

U.S. PATENT DOCUMENTS 6,316,254 B1 * 11/2001 Kaushansky .................. 435/325
7,345,019 B1 * 3/2008 Brines et al. ...................... 514/2

OTHER PUBLICATIONS

Liu et al. Thrombopoietin has a differentiative effect on late-state human erythropoiesis. British Journal of Haematology, vol. 105:459-469 (1999).*
Boissel et al. Erythropoietin structure-function relationships. The Journal of Biological Chemistry, vol. 268, No. 21:15983-15993 (1993).*
Chern et al. Structure role of amino acids 99-110 in recombinant human erythropoietin. European Journal of Biochemistry, vol. 202:225-229 (1991).*
Mitra et al. N-linked oligosaccharides as outfitters for glycoprotein folding, form and function. TRENDS in Biochemical Sciences, vol. 13 No. 3:156-163 (2006).*
Shigekazu Haruki, Special Topic Research of Hallucination Recent Advance III. Special Hallucination, Surrounding Phenomena Dialysis and Hallucination From the Standpoint of Liaison Psychiatry, Journal of Clinical Psychiatry, Japan, 1998, vol. 27, No. 7, pp. 923-933. (Eng. Translation Abstract of Clinical Psychiatry 27 (7):923-933).
Steinberg, H., et al., Erythropoietin and Visual Hallucinations in Patients on Dialysis, Psychosomatics, Nov. 1996, vol. 37, p. 556-563.
Tokinaga, N., et al., Hallucinations After a Therapeutic Dose of Benzodiazepine Hypnotics with Co-administration of Erythromycin, Psychiatry and Clinical Neurosciences, 1996, vol. 50, p. 337-339.

* cited by examiner

*Primary Examiner* — Elizabeth C Kemmerer
*Assistant Examiner* — Regina M DeBerry
(74) *Attorney, Agent, or Firm* — Marshall & Melhorn, LLC

(57) ABSTRACT

Method for treatment and/or prophylaxis of schizophrenia and related psychoses of a human being, erythropoietin being administered to the human being.

8 Claims, 13 Drawing Sheets

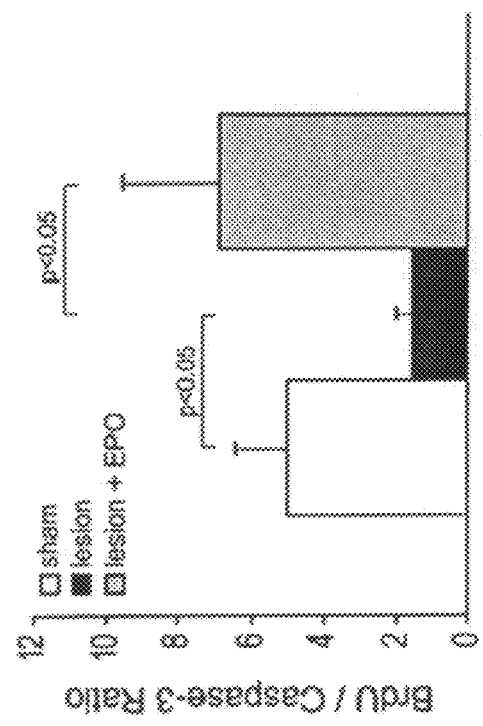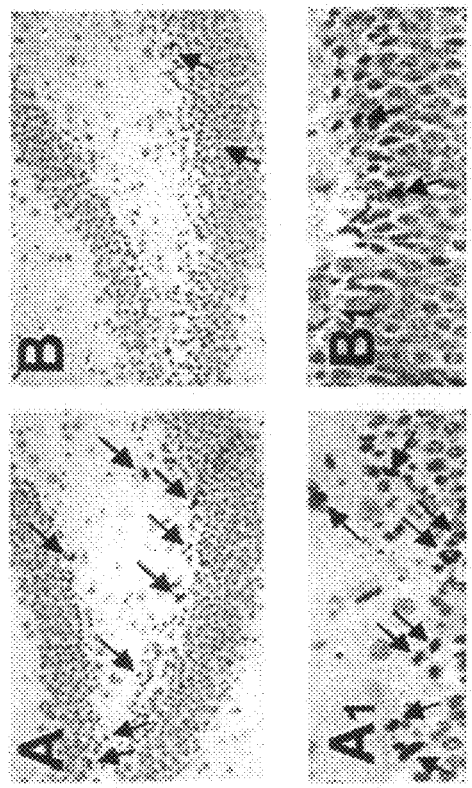
FIG. 3

USE OF ERYTHROPOIETIN AND SUBSTANCES INCREASING AND/OR PROLONGING THE ACTIVATION AND/OR STIMULATION OF ERYTHROPOIETIN RECEPTORS FOR TREATING AND/OR PREVENTING SCHIZOPHRENIA AND RELATED PSYCHOSES

RELATED APPLICATIONS

This application is a continuation-in-part of U.S. patent application Ser. No. 10/363,617, filed on Jun. 17, 2003, now abandoned entitled "Method for treating schizophrenia and related psychoses, and the use of erythropoietin or erythropoietin derivatives for treating schizophrenia disorders and related psychoses," which is incorporated herein by reference. Application Ser. No. 10/363,617, now abandoned, was pending as of the filing date of the present application.

FIELD OF THE INVENTION

The present invention relates to a method for treating and/or preventing schizophrenia and related psychoses, subsumed in the following under "schizophrenia.

BACKGROUND OF THE INVENTION

The etiology and pathogenesis of schizophrenia in the sense of the above definition are to date unknown. In fact there is agreement about the important role of genetic influences, however a series of presumably relevant co-factors is known, for example neurotrauma, drug consumption etc. which appear to have an influence on the outbreak of the disease. In particular the molecular and cellular mechanisms which play a role pathogenetically in this disease are also unknown. No really good animal models for schizophrenia have therefore been produced to date. The available animal models cover merely partial aspects of the disease.

It is therefore the object of the present invention to make available a method for treating schizophrenia and related psychoses and also a means for treating schizophrenia and related psychoses.

This object preferably is achieved by the characterizing features of the present invention. Advantageous embodiments and further developments of the solution will be apparent from the description of the invention provided herein.

There is thereby understood by schizophrenia actual and/or chronic schizophrenia and related psychoses. By treatment there should be considered not only the treatment in the case of symptoms which have already occurred but also the prophylactic use in the case of people who are particularly at risk, for example in the case of people with a high hereditary factor, with neurotrauma (e.g. brain injury), psychotrauma and the like.

The proposed medicinal neuroprotection in schizophrenia is thereby a generally completely new therapeutic and prophylactic starting point. This takes into account the observation confirmed again and again by epidemiologists and clinicians that, already in the course of the first episode of the disease, a dramatic impairment of cognitive/mental function happens which is at least partially irreversible and levels off generally in the further episodes rather on a constant or a less progressive level. Here now the consistent use of a neuroprotective therapy approach intervenes also as "add-on therapy" in conjunction with a symptom-arresting neuroleptic, particularly in the first episode of the psychosis. A preventive use of erythropoietin in the people particularly at risk is also proposed according to this invention.

Evidence of the importance of the use of erythropoietin (EPO) as means of prevention of schizophrenia and related psychoses has been further established in recent scientific literature published by the inventor. Both publications are incorporated herein by reference. Sirén A.-L., Radyushkin K., Boretius S., Kämmer D., Riechers C.-C., Natt O., Sargin D., Takashi W., Sperling S., Michaelis T., Price J., Meyer B., Frahm J. and Ehrenreich H., Brain 129: 480-89 (2006) show that EPO can prevent global brain atrophy after unilateral parietal lesion in the mammalian brain (mouse model). EPO given to lesioned animals abolished the cognitive dysfunction, as tested, for example, by the Morris water maze task, seen in animals not administered EPO.

In conjunction with the shown results in an animal, the inventor has also published the results of EPO administration in chronic schizophrenic patients (Ehrenreich H., Hinze-Selch D., Stawicki S., Aust C., Knolle-Veentjer S., Wilms S., Heinz G., Erdag S., Jahn H., Degner D., Ritzen M., Mohr A., Wagner M., Schneider U., Bohn M., Huber M., Czernik A., Pollmächer T., Maier W., Siren A.-L., Klosterkötter J., Falkai P., Rüther E., Aldenhoff J. B. and Krampe H., Molecular Psychiatry 12:206-220 (2007). The use of recombinant human EPO at dosages proscribed in the parent application, once a week for 12 weeks resulted in improved cognitive function, as measured, for example, by the Repeatable Battery for the Assessment of Neuropsychological Status (RBANS) in these patients.

These published studies were carried out to show a "proof-of-principle." It should be clear that the invention outlined in the parent application and the further inventive claims of this continuation-in-part (CIP) are not only plausible, but very promising tools in the treatment and prevention of schizophrenia and its related psychoses.

Erythropoietin, also described in brief as "EPO", is a glycoprotein occurring naturally in the body with a molecular weight of 34,000 daltons (W. Jelkmann, "Erythropoietin: Structure, Control of Production, and Function", Physiological Reviews, 1992, Volume 72, pages 449 to 489). It is an essential growth factor for the production of erythrocytes and was isolated for the first time already in 1977.

There are a plethora of substances, which all are considered to increase or prolong the activation and/or stimulation of erythropoietin receptors. Besides erythropoietin itself, whether native or recombinant, whether in native sequence or even after sequence changes or sequence shortening, erythropoietin analogs, erythropoietin fragments or erythropoietin agonists were developed. As examples for recombinant EPO, Epoetin a (Epogen by Amgen Inc., Procrit by Ortho Biotech Inc., Johnson and Johnson Inc.), Epoetin β (Neorecormon by Hoffmann-LaRoche AG) and Epoetin ω (Epomax), Epoetin δ (DynEpo, Shire Pharmaceuticals Group Plc.) with varying glycosilation and sialysation are known. Genetically modified EPO are known as Darbepoetin α (Amgen Inc.) and CERA (Hoffmann-LaRoche AG). Further, erythropoietin receptor activating antibody (e.g. by Abbott), fusion proteins like Epo-Fc and carbamylated EPO (CEPO, Lundbeck A/S) are known. Further, endogenous erythropoietin stimulating substances, substances increasing the release and/or activity of endogenous erythropoietin (e.g. HIF-stabilizers, e.g. by Fibrogen Inc. or Torrent Pharmaceuticals Ltd.) are also known. Furthermore, erythropoietin analogs or mimetics are known, e.g. SEP (Synthetic Erythropoiese Protein by Gryphon Therapeutics) or Hematide (by Affymax Inc.) and others known as EPO-analogs or -mimetics by AplaGen. It is even known to transfer the gene coding for erythropoietin into a patient in order to express erythropoietin.

All of these substances are known to increase and/or prolong the activation and/or stimulation of the EPO receptor besides their antiapoptotic, tissueprotective effect. Some useable EPO variants are published for example in the following publications, which are incorporated herein by reference:

Leist et al., Science 2004, Vol. 305, pp. 239-242, WO 86/03520, WO 85/02610, WO 90/11354, WO 91/06667, WO 91/09955, WO 93/09222, WO 94/12650, WO 95/31560. WO 95/05465.

Also, incorporated herein by reference is an overview of known variants, analogs, mimetics and equivalents which can also be used in their entirety in the present invention and also of known fields of use thereof appears in Brines and Cerami, Nature Review, Neuroscience, June 2005, Vol. 6, pp. 484-494.

The term erythropoietin in the scope of this invention is meant to describe any agent that increases and/or prolongs the activation and/or stimulation of any kind of erythropoietin receptor. This would include any of the substances described or referenced above.

Erythropoietin has been in frequent clinical use for many years in nephrodialysis in the case of patients who have renal anemia, for obtaining fairly large quantities of autologous blood before planned operations and it also hit the press headlines as a sports drug.

Erythropoietin thereby proved to be exceptionally well tolerated. In particular, the frequently therapeutically desired stimulation of the hematopoiesis with polyglobulin and also an arterial hypertonia which is rarely to be seen should be mentioned as a relevant side-effect. Both effects are to be expected mainly after chronic erythropoietin administration. These are remedied when required relatively simply by medicinal treatment or blood-letting. Intolerance reactions or anaphylactic reactions in the case of erythropoietin constitute rarities.

As a fairly large protein with a molecular weight of approximately 34,000 daltons erythropoietin is considered as generally not being able to easily surmount the blood-brain barrier. A directly intracerebroventricular administration of erythropoietin, i.e. direct infusion of erythropoietin into the brain tissue is ruled out however in human beings usually, because of risks which are involved in the installation and the maintenance of a temporary ventricular drainage, such as infections or hemorrhages.

SUMMARY OF INVENTION

It has been detected that the blood-brain barrier, in the case of an acute phase of a psychosis as well as in the case of an intact blood-brain barrier, is sufficiently permeable for erythropoietin to allow a therapeutically effective amount of erythropoietin to cross the blood brain barrier. Hence a systemic peripheral administration, for example parenterally as well as vascularly, intranasally, per inhalation, in particularly intravenously, subcutaneously and/or intramuscularly (for example for depot type), of erythropoietin is nevertheless successful.

The invention also comprises a step where erythropoietin is administered in a dose of 5,000 IU to 500,000 IU per administration and/or per day and/or per week. In another embodiment the invention comprises a step where erythropoietin is administered in a dose of 5,000 IU to 200,000 IU per administration and/or per day and/or per week. In another embodiment, the invention comprises a step where erythropoietin is administered in a dose of 5,000 IU to 50,000 IU per administration and/or per day and/or per week. A further embodiment of the invention comprises a step where erythropoietin is administered in a dose of 5,000 IU to 35,000 IU per administration and/or per day and/or per week. A still further embodiment of the invention comprises a step where erythropoietin is administered in a dose of 35,000 IU per administration and/or day.

In the case of a chronic treatment or long-term therapy, a slow effect of the administration of erythropoietin takes place as long as, with persistently high blood levels (by administration of up to 200,000 IU per week) of erythropoietin, a crossing of erythropoietin via the blood-brain barrier into the brain takes place nevertheless despite the intact blood-brain barrier.

Due to this surprising crossing of erythropoietin into the brain in the case of the acute and/or chronic phase of a psychosis, erythropoietin can be used in order to influence all three mechanisms potentially involved in the pathogenesis of the schizophrenia, said mechanisms resulting in a neuronal dysfunction: these are apoptosis, the metabolic disorder of the nerve cells and also the synaptic junctions/axon sprouting.

It can be established in summary that medicinal neuroprotection in the case of schizophrenia (acute and/or chronic) or in the case of risk of schizophrenia is generally a completely new therapeutic and prophylactic approach.

A few examples of the methods according to the invention and the results thereof are shown in the following.

BRIEF DESCRIPTION OF THE DRAWINGS

FIG. 2A shows the lesion maker with a tip diameter of 1 mm. FIG. 2B-D shows evolution of lesion on hematoxylin-eosin stained sections, at 24 h (B,C) and 9 months (D) after lesioning. FIG. 2E, F shows the lesion is visible at 3 months in MRI as a small indentation on the cortical surface. FIGS. 2G-J shows an illustration of Evans-Blue albumin leakage (as indicator of blood-brain-barrier breakdown) 30 min (G,H) and 24 h (I,J) after lesion. FIG. 2K, L Ongoing apoptosis at 24 h is evident as cleaved caspase-3 (K) and TUNEL positive (L) cells surrounding the lesion.

FIG. 3 shows the ratio of cell proliferation to cell death in the dentate 24 h after unilateral cortical lesion. Many bromodeoxyuridine (BrdU) (FIG. 3A, $A_1$) and few cleaved caspase-3 (FIG. 3B, $B_1$) positive cells in the contralateral dentate of an EPO-treated animal at 24 h after lesion. FIG. 3C shows BrdU/cleaved caspase-3 ratio calculated using bilateral dentate cell counts 24 h after lesion; n=5-7.

FIG. 5A shows brain matter reduction and FIG. 5B shows ventricular enlargement as revealed by in vivo 3D MRI at 3 and 9 months after unilateral parietal cortical lesion and their prevention by EPO. FIG. 5C shows representative T1-weighted MR images (117 μm isotropic resolution) at 9 months survival time point of a sham, lesion, and lesion+EPO mouse brain demonstrating ventricular enlargement and global increase in liquor space upon lesion.

FIG. 6A, B show performance in open field at (A) 3 months and (B) 9 months after lesion. FIG. 6C shows number of head dips in the hole board test and FIG. 6D shows percent of open arm entries in the elevated plus-maze are significantly increased in lesioned as compared to sham-operated or lesion+EPO groups.

FIG. 7A, B show the latency to find the hidden platform and, as insert, the number of visits to the target site in the probe trial (platform removed) on day 9 in sham, lesion and lesion+EPO groups. FIG. 7C, D show the latency to find the visible platform of these mice.

FIG. 8C shows number of head dips in the hole board test and ventricular size in MRI are not different in the 3 groups at 3 months after occipital lesion.

FIG. 9A shows body weight development during EPO/placebo infusions immediately following setting of the lesion. FIG. 9B shows body weight 3 months and 9 months after setting the lesion.

DESCRIPTION OF THE PREFERRED EMBODIMENTS

Figure 1:
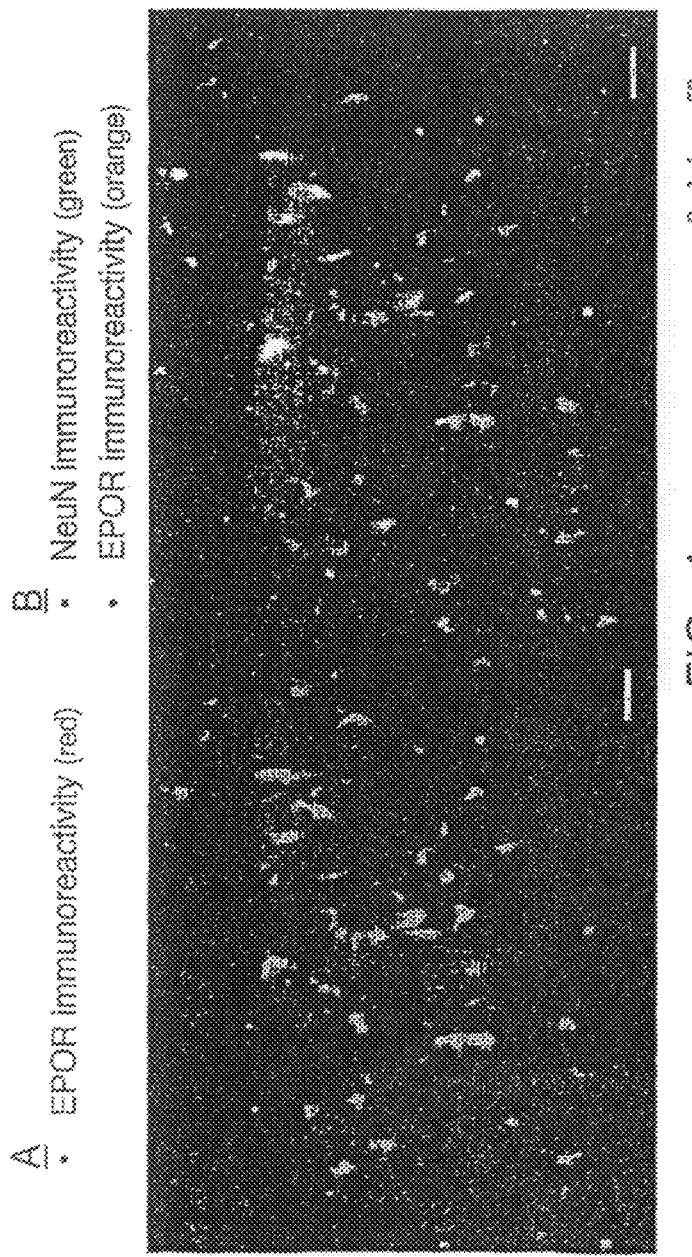
FIG. 1A and FIG. 1B show immunohistochemical examinations of sections of the brain of schizophrenics.

The present invention relates to global brain atrophy after unilateral parietal lesion and its prevention by erythropoietin. To model discrete brain injury that may predispose to late neurodegenerative changes, we developed a cryolesion procedure of the parietal cortex in juvenile (4 week-old) mice. We induced the lesion by freezing through the skull bone with a liquid nitrogen-cooled copper cone with a tip diameter of 1 mm (FIG. 2a). We discovered that freezing for 60 s produces a highly reproducible lesion that evolves over time, reaching a maximum diameter 24 h after freezing (FIGS. 2b-2c). This lesion is replaced over time by a fibrous scar in the parietal gray matter (FIG. 2d), which is barely visible by high-resolution three-dimensional magnetic resonance imaging (MRI) at 3 months (FIGS. 2e-2f, arrows). Transient leakage of the blood brain barrier most likely contributes to the neurodegenerative process. This leakage is maximal 24 h after setting of the lesion and extends over the entire hemisphere to the contralateral white matter (illustrated in FIGS. 2g-2j). The primary cortical lesion, however, is always restricted to the parietal cortex, with apoptotic cells within and surrounding the lesion during its acute evolution (FIGS. 2k, 2l).

We next addressed whether this discrete parietal lesion had more global effects on brain anatomy. In previous studies we provided evidence for a profound microglial activation and strong inflammatory cytokine expression that were not restricted to the lesion perimeter in the right parietal cortex but were seen bilaterally in the hippocampus hours to days after unilateral cryolesion (Knerlich et al., 1999; Sirén et al., 2000). The hippocampal dentate gyrus harbors progenitor cells that are capable of proliferation and neuronal differentiation and respond to brain injury (Arvidsson et al., 2002; Wang et al., 2004; Yoshimura et al., 2003). Neuroinflammation in the dentate inhibits proliferation of progenitor cells (Monje et al., 2003). Disruption of adult neurogenesis in the dentate, in turn, prevents some forms of associative learning (Shors et al., 2001) and the level of dentate neurogenesis seems to correlate with spatial memory performance in aged rats (Drapeau et al., 2003). We hypothesized that the capacity of cellular self-renewal in the dentate hilus is crucial for longterm functional recovery after lesioning. Therefore, acute changes in the ratio of cell proliferation to cell death in the dentate were monitored after the lesion. As early as 24 h after placing the unilateral cortical lesion, we observed a bilateral reduction in the ratio cell proliferation to cell death (quantified here as a "BrdU/cleaved-caspase-3" ratio) in the hilar region of the dentate (FIGS. 3a-3c).

Hematopoietic growth factors that pass the blood-brain-barrier have shown striking effects on proliferation and survival of newly generated neurons (Ehrenreich et al., 2005; Shingo et al., 2001; Wang et al., 2004; Yoshimura et al., 2003). We therefore expected a peripheral application of recombinant erythropoietin (EPO) to modulate the cellular response to brain injury. EPO is a hematopoietic growth factor with a 20-year history of safe clinical application, and has been identified as a potent neuroprotective agent in vitro and in vivo (Bernaudin et al., 1999; Brines et al., 2000; Ehrenreich, 2004; Ehrenreich et al., 2004; Sakanaka et al., 1998; Sirén et al., 2001). Its neuroprotective profile is unusually complex with antiapoptotic, antioxidant, antiinflammatory, stem cell modulatory, neurotrophic, and angiogenetic properties, that collectively reflect a non-hematopoietic function of EPO in brain development, presumably during phases of physiological hypoxia (Ehrenreich et al., 2005; Shingo et al., 2001; Sirén et al., 2001; Wang et al., 2004). These properties may explain its powerful effect in entirely different neurological disease models, ranging from acute stroke to chronic conditions like experimental autoimmune encephalitis (EAE) or diabetic neuropathy (Agnello et al., 2002; Bernaudin et al., 1999; Bianchi et al., 2004; Brines et al., 2000; Diem et al., 2004; Ehrenreich et al., 2002; Sakanaka et al., 1998). At the cellular level, EPO binds to a specific receptor of the cytokine type I receptor superfamily, which in the brain may consist of heteromeric subunits (Brines and Cerami, 2005). Molecular mechanisms of action of EPO in the nervous system include phosphorylation of Akt, ERK1/2, Stat5 and activation of NFkappaB (Brines and Cerami, 2005; Digicaylioglu and Lipton, 2001; Sirén et al., 2001).

When recombinant human EPO (rhEPO, 5 U/g intraperitoneally) was given only once, i.e. immediately after setting of the parietal lesion in mice, the detected "imbalance" of cell proliferation and cell death, as measured after 24 hours in the dentate gyrus, was fully prevented (FIG. 3c). In agreement with these findings, increased neurogenesis by EPO during brain development and after injury has been demonstrated by several independent groups (Shingo et al., 2001; Wang et al., 2004; Yu et al., 2002). Apart from a direct stimulation of neurogenesis, the antiapoptotic and anti-inflammatory (Agnello et al., 2002; Brines and Cerami, 2005; Sirén et al., 2001) properties of EPO most probably contributed to its favorable effect on the cell proliferation/cell death ratio. In fact, caspase inhibitors increased survival of newly formed BrdU-labelled cells in the dentate gyrus following epileptic seizures (Ekdahl et al., 2001) and antiinflammation can be expected to partly restore neurogenesis in the dentate after injury (Arvidsson et al., 2002; Magavi et al., 2000; Monje et al., 2002; Monje et al., 2003).

To explore whether a similar reduction of neurons in the dentate hilar region could still be observed at later time points, we determined the spatial density of neurons in this area several months after a unilateral parietal cortex lesion. In this experiment, mice were treated with rhEPO (5 U/g intraperitoneally) every other day, for a total of 14 days, and their brains were analyzed after 3 months. As summarized in FIG. 4, dentate hilus neurons were significantly reduced in number in both hemispheres of the lesioned mice, and this bilateral cell loss was again efficiently prevented by prior administration of rhEPO.

As shown in this study, a unilateral parietal lesion reduces via as yet unknown mechanisms also the capacity of the contralateral dentate for renewal of cells. Assuming that a minimum amount of trophic factors and the generation of new cells is necessary to maintain the normal dimensions of the cortex, any disturbance of this equilibrium, along with post-traumatic acceleration of neurodegenerative processes, may contribute to global cortical atrophy. In fact, gray matter reduction and ventricular enlargement (revealed by MRI) take place after traumatic brain injury and correlate with human cognitive and functional outcome (MacKenzie et al., 2002; Parker and Rosenblum, 1996).

We thus tested the hypothesis, that brain atrophy would be seen several months after applying a parietal cortical lesion, and that a neuroprotective treatment with EPO prevents brain tissue loss, similar to EPO's ability to reduce cell loss in the dentate hilar region. Definition of global brain atrophy both in mice and man includes decreased total brain matter volume and increased ventricular size which can be visualized and quantified by MRI (Delatour et al., 2005; MacKenzie et al., 2002; Redwine et al., 2003; Resnick et al., 2003; Rusinek et al., 2003; Schott et al., 2005). Indeed, when monitored by three-dimensional MRI, a global reduction in brain matter and a bilateral enlargement of brain ventricles was evident at both 3 months and 9 months after parietal lesion (FIGS. 5a-5c).

Symmetry, magnitude, and localization of these volume changes had features of "premature brain aging" (Nemetz et al., 1999; Resnick et al., 2003; Rusinek et al., 2003). The tissue loss may well be additive to the normal aging effect that could be independently demonstrated in this experiment by a comparison of sham operated mice at the 3 and 9 months time point (FIGS. 5a, 5b). The magnitude of ventricular enlargement and brain matter loss after parietal lesion in our study is comparable with the age-dependent brain atrophy in APP/PS1 transgenic mice, a mouse model of Alzheimer's disease (Delatour et al., 2005).

Importantly, early EPO treatment for 14 days, beginning immediately after lesioning, prevented brain atrophy monitored 9 months later. Brain matter volume and ventricle size in the EPO treated mice after 9 months survival time was nearly identical to that of sham operated animals, but significantly different from lesioned placebo-treated mice (FIGS. 5a-5c).

In humans, functional consequences of brain atrophy are cognitive impairments, behavioral alterations, and emotional deficits (Benedict et al., 2004; Parker and Rosenblum, 1996; Rusinek et al., 2003). We tested mice in all experimental groups using an extensive behavioral test battery over 2 weeks to explore whether morphological signs of neurodegeneration are translated into functional impairments. As expected from the discrete parietal localization and small size of the lesion (FIG. 1), no impairments of motor performance in Rota-Rod (data not shown) or open field (FIGS. 6a-6b) were detected at any time point after lesion. Thus, neither the selective changes in exploration- and activity-related behavior (hole board, elevated plus-maze), detectable 3 and 9 months after parietal lesion (FIGS. 6c, 6d), nor the impaired Morris water maze performance at 9 months (FIGS. 7a, 7b) were related to an underlying motor disability of performing these tests.

Specifically, we observed a significantly increased exploratory behavior in the hole-board test at 3 months after unilateral cortical lesion, generally considered a test of exploratory behavior and (hyper)activity in mice. This abnormal test result showed a spontaneous partial recovery after 9 months (FIG. 6c). A contralateral hemispheric compensation in this task is likely to explain this recuperation. Indeed, when both parietal cortices were lesioned simultaneously, the number of abnormally increased head dips persisted (with 15±2 head dips in bilaterally lesioned mice as compared to 7±1 and 9±2 head dips in sham operated and unilaterally lesioned mice, n=10-19, respectively).

Open arm entries in the elevated plus-maze (a measure of motor activity) were distinctly increased after 3 months in lesioned mice. In contrast, the time spent in open arms (a measure of fear-related behavior) was not different in lesioned and sham-operated mice (61±7% and 50±6%, respectively, n=10, p=0.2). At 9 months, entries were highly reduced in all experimental groups (FIG. 6d). In contrast, a significantly impaired spatial learning ability of lesioned mice in Morris water maze did not become evident before 9 months after brain injury (FIGS. 7a, 7b). Therefore, age-related degeneration/gray matter loss obviously added to the lesion-induced degeneration, resulting in clear spatial learning deficits which are still compensated for in younger animals. However, in the visual platform paradigm, a simple target recognition test, all groups at a respective time point performed equally (FIGS. 7c, 7d).

Prepulse inhibition (PPI), a test of sensorimotor gating, considered to be affected in schizophrenia (Braff et al., 2001), showed a distinct reduction in lesioned mice (FIG. 8a). Inasmuch as this test is non-specific for schizophrenia but found impaired in many other conditions (Braff et al., 2001), we saw it not only reduced after right parietal but also after left occipital lesion (FIG. 8b). In contrast, neither hole board performance nor ventricular size are affected by lesioning the occipital cortex (FIG. 8c).

Figure 6:
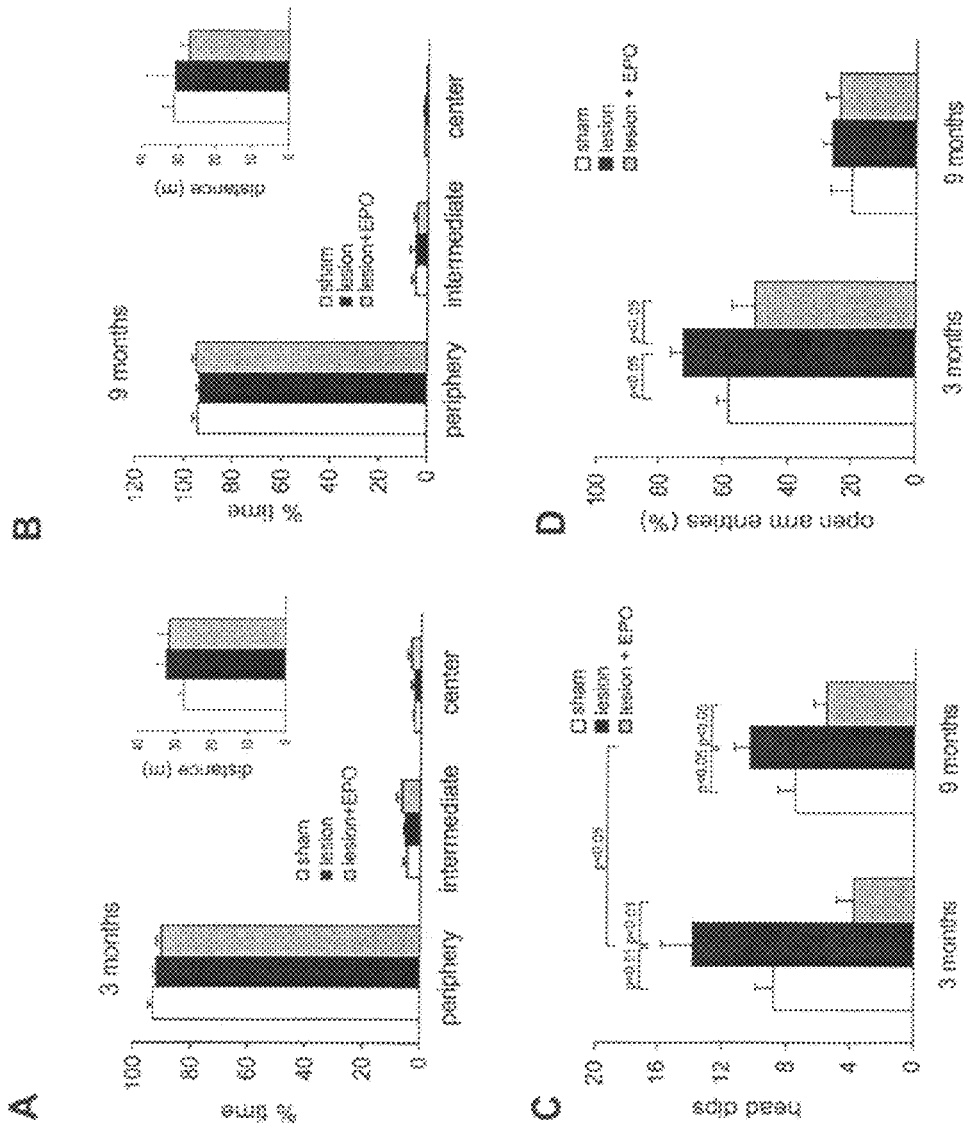
FIG. 6 shows behavioral follow-up 3 and 9 months after unilateral parietal cortical lesion in mice.
Figure 7:
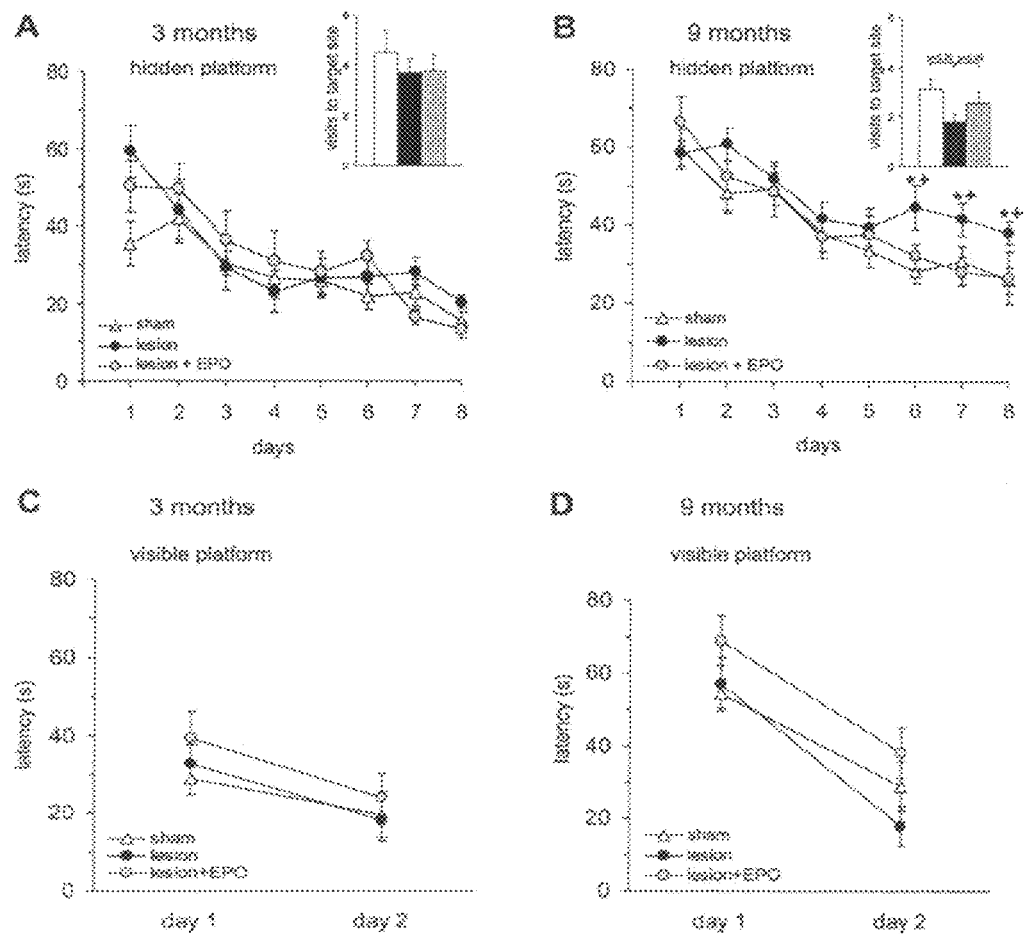
FIG. 7 shows performance in Morris-Water-Maze 3 and 9 months after unilateral parietal cortical lesion in mice.
Figure 8:
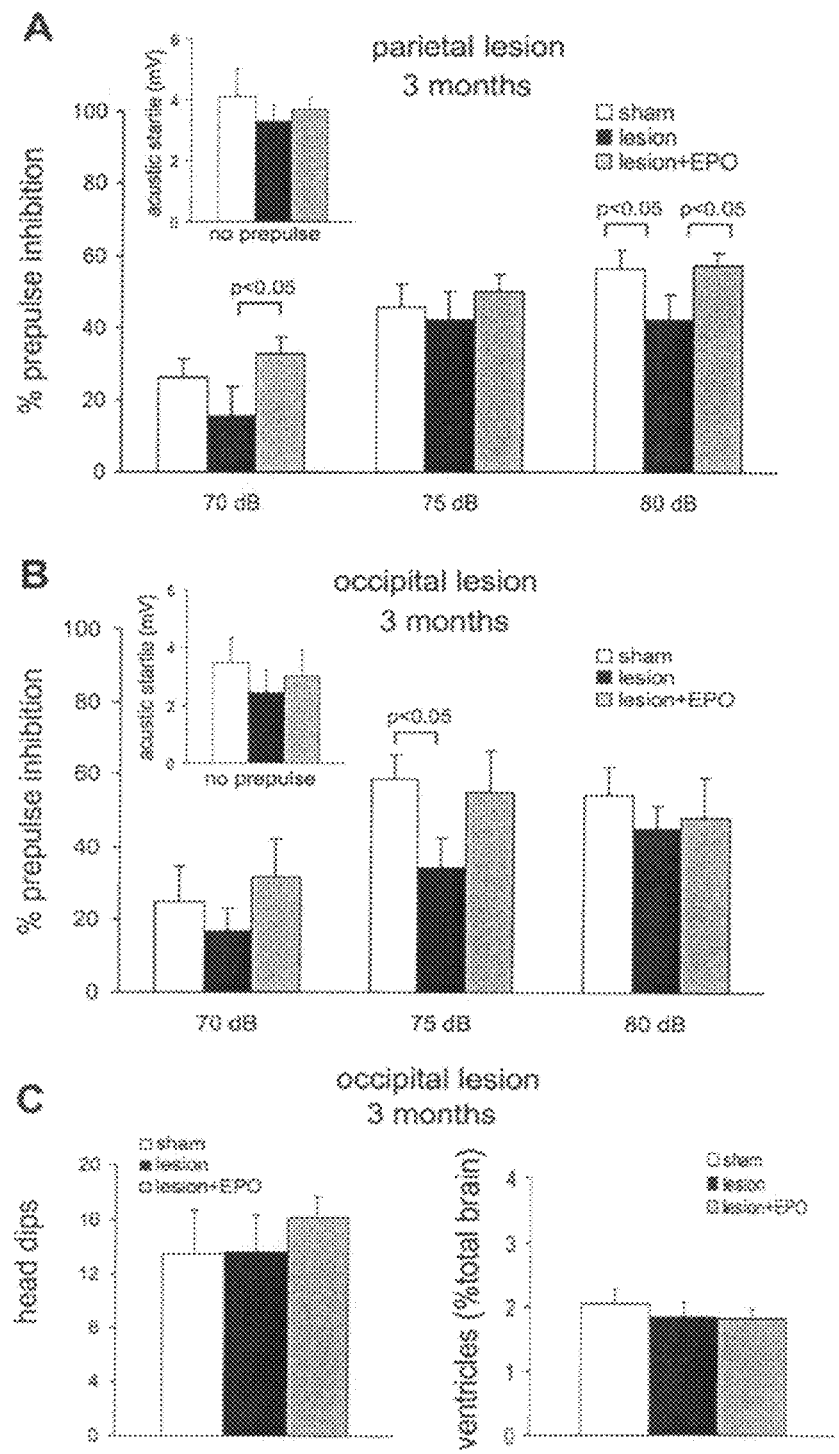
FIG. 8 shows behavioral follow-up 3 months after unilateral parietal or occipital cortical lesion in mice. Prepulse inhibition is attenuated in lesioned as compared to sham-operated or lesion+EPO treated groups both after parietal (as shown in FIG. 8A) and occipital (as shown in FIG. 8B) cortical lesion and, as insert, the magnitude of acoustic startle without prepulse in sham, lesion and lesion+EPO groups.

We next tested whether, similar to the morphological consequences, the behavioral alterations set forth by the unilateral parietal cortex lesion were preventable by early neuroprotective therapy with EPO. We discovered that both the lesion-induced atypical behavior in hole board and elevated plus maze as well as the only later evident spatial learning deficit in Morris water maze at 9 months were abolished by EPO, as was the reduced prepulse inhibition (FIGS. 6-8). Thus, a circumscribed parietal lesion in the young mouse leads to significant alterations in behavior in the mature animal, and these changes can be blocked by the neuroprotective agent, EPO, delivered in the intervening period.

Interesting and yet unclear is the reduction in head dips in lesioned, EPO treated mice as compared to sham operated mice ($p \leq 0.01$). The test measures exploration behavior and (hyper)activity. It could potentially be influenced by the level of anxiety. In our mice, however, elevated plus maze (time spent in open arms—see above) and open field behavior (FIGS. 6a, 6b) point against this possibility.

We note again that overall motor performance (Rota-Rod, open field) of EPO treated mice was not different from that of control mice at any time point tested. There were also no differences in blood hematocrit levels in the EPO treated mice compared to placebo-treated or sham operated mice at the time of testing at 3 months after setting of the lesion (41±2%, 42±2% and 40±2%, n=8, respectively). As expected, blood hematocrit was elevated immediately after 14-days of EPO injections (57±3%, n=5) as compared to placebo treated mice (38±1%, n=5, $p<0.05$) but returned to normal levels already within 4-weeks after cessation of EPO therapy (38±2% versus 40±2%, n=5, not significant). As a general health indication, body weight was not different in sham, lesion, and lesion+EPO groups (FIGS. 9a, 9b).

Taken together, in this report, we made the surprising observation that a discrete lesion to the parietal cortex of juvenile mice, i.e. during brain maturation, is by itself the primary cause of a global neurodegeneration, with significant changes in brain morphology and function upon longterm follow-up. Such exogenously evoked neurodegeneration resembles 'premature' aging and might help to explain how degenerative processes that begin in the parietal lobe (as found in childhood onset schizophrenia (Thompson et al., 2001) can spread over the entire brain. Our data also indicate that brain trauma is likely to accelerate, or even to induce, those neuropsychiatric disorders that have a progressive degenerative component, such as Alzheimer's disease or schizophrenia. Although the molecular details of the underlying spreading mechanisms need to be defined, we provide proof-of-principle that the critical downstream events of experimental brain trauma can be efficiently prevented by EPO-mediated neuroprotection. These findings suggest that prophylactic therapies should be considered to prevent some of the late consequences of brain injury.

Materials and Methods

All experiments were approved by and conducted in accordance with the regulations of the local Animal Care and Use Committee.

Surgery: Four-week old male C57BL6 mice were anesthetized with an intraperitoneal (i.p.) injection of 0.25% tribromoethanol (Avertin) (0.125 mg/g). The parietal skull was exposed through a scalp incision and a freezing lesion was placed on the right parietal cortex (unilateral lesions) or on both parietal cortices (bilateral lesions) (coordinates from bregma: 1.5 mm posterior, 1.5 mm lateral). For lesions on the left occipital cortex, the following coordinates from bregma were used: 3.0 mm posterior, 1.5 mm lateral. A cone-shaped copper cylinder with tip diameter of 1 mm was cooled with liquid nitrogen (−183° C.). Its tip was stereotaxically placed in direct contact with the exposed parietal/occipital skull and kept in place for 60 s. Sham-operated animals went through the same procedure without cooling the metal cone. We injected EPO (epoetin-alpha, Janssen-Cilag, Neuss, Germany, 5 U/g, i.p.) or placebo (diluent for EPO, 0.01 ml/g, i.p.) immediately after setting of the lesion, and every other day for 14 days thereof. In a separate group of mice, bromodeoxyuridine (BrdU, 10 μg/g, i.p. Boehringer, Mannheim, Germany) was injected immediately following the lesion and the brains were removed after 30 min or 24 h.

Histology and immunohistochemistry: Extravasation of albumin-bound Evans-Blue (0.3 ml/mouse of a 2% solution in 0.9% NaCl, Sigma, Deisenhofen, Germany) through the blood-brain-barrier was evaluated after 30 min and 24 hours. We used paraformaldehyde-fixed paraffin-embedded tissue for all histology and immunohistochemistry. Tissue-sections were boiled in citrate buffer, washed in phosphate-buffered saline (PBS), blocked in 10% horse serum and exposed overnight at 4° C. to mouse anti-bromodeoxyuridine (BrdU, Chemicon, Temecula, Calif., USA, 1:10 000), or rabbit anti-cleaved caspase-3 (Cell Signaling, Frankfurt a.M., Germany) antibodies (1:1000 in 2% horse sera/PBS). The staining was visualized using a peroxidase-labeled-avidin-biotin kit (Vector Laboratories, Burlingame, Calif., USA). The In Situ Cell Death detection kit (Roche Diagnostics, Penzberg, Germany) was used for detection of apoptosis with the TUNEL-method. For each mouse, at least 4 separate randomly sampled coronal sections throughout the dorsal hippocampus were used for counting the number of BrdU-labeled, cleaved caspase-3-positive or surviving cells on hematoxylin-eosin stained sections in the dentate hilus using a Zeiss-Axioplan microscope (Zeiss, Jena, Germany), and the cell numbers were expressed as cell counts/0.1 mm. All cell counting was performed by independent raters blinded to treatment condition.

Magnetic resonance imaging (MRI): Upon completion of the behavioral analysis, the mice were anesthetized with ketamine/xylazine (0.1 mg/0.015 mg/g, i.p.), intubated, and kept under anesthesia with 1-1.5% halothane in 70:30 $N_2O:O_2$. In vivo brain volumetry was performed by MRI at a field strength of 2.35 T (Bruker Biospin, Ettlingen, Germany) using a T1-weighted 3D FLASH sequence as previously described (Natt et al., 2002). We determined the total brain volume (excluding bulbus olfactorius, cerebellum, and brain stem) (=T) and the size of the lateral ventricles (=V) by manually drawing respective regions-of-interest on up to 50 contiguous horizontal MRI sections (117 μm thickness). Brain matter (=M) is calculated by subtraction of ventricle volume from total brain volume (M=T−V). The analysis was blinded for sham operated, lesioned, and EPO-treated animals.

Behavioral testing: Animals were tested in a battery of behavioral tests including hole-board, elevated-plus-maze, Morris-water-maze, Rota-Rod, and open field at 3 months (n=30) and 9 months (n=30) after setting of the cortical lesion. In addition, prepulse inhibition and hole-board test were performed 3 months after parietal or occipital cortical lesioning (n=7–13). All testing was done in a sound-attenuated room.

Hole-board test: Each mouse was placed in the center of the hole-board (21×21×36 cm transparent Perspex chamber with nontransparent floor raised 5 cm above the bottom of the chamber with 12 equally spaced holes, 2 cm in diameter) and allowed to explore the chamber for 3 min. The distance traveled and number of holes explored (=head dips) were monitored by two layers of infrared photo beams connected to a computer equipped with the "AKS" software (TSE, Bad Homburg, Germany).

Elevated-plus-maze: The animal was placed in the central platform facing an open arm of the plus maze (made of gray Perspex with a central 5×5 cm central platform, 2 open arms, 30×5 cm, 2 enclosed arms, 30×5×15 cm, illumination ~300 Lux). Behavior was recorded by an overhead video camera and a PC equipped with "VideoMot 2" (TSE) software to calculate the time each animal spent on open or closed arms. The proportion of time spent in open arms was used for estimation of open arm aversion (fear equivalent). The frequency of open arm entries was determined as a measure of motor activity.

Morris-water-maze: Spatial learning and memory was assessed in a water-maze (Morris, 1984) consisting of a large circular tank (diameter 1.2 m, depth 0.4 m) containing opaque water (25±1° C., depth 0.3 m). To escape from water, mice had to find a hidden platform (9×9 cm) submerged approximately 1 cm below the surface. The pool was located on an elevated platform 50 cm above the floor in a special well-lit room with white walls. Swim paths were monitored by a PC linked video camera mounted on the ceiling. The coordinates of the animal's position were sampled in real-time by "VideoMot 2" software (TSE) that provided measures of escape latency, swim speed and path length during acquisition and, during the probe trial, the number of visits to each quadrant of the maze. In the visible platform task, the platform was cued by means of a 15 cm high black flag mounted on it and placed pseudo-randomly in different locations across trials. The cued training was performed in the room without prominent extra-maze cues on the walls. Mice had 4 trials per day for 2 days and escape latency was measured. For spatial training (hidden platform), extra-maze cues were mounted on the walls. The platform was located at the center of one of the four quadrants of the pool. Mice were trained to find the hidden escape platform, which remained in a fixed location throughout testing. They received 4 trials per day for 8 days, with an inter-trial interval of ~5 min. The mice were placed into the pool facing the side wall randomly at one of 4 start locations, and allowed to swim until they found the platform, or for a maximum of 90 s. Any mouse that failed to find the platform within 90 s was guided to the platform. The animal then remained on the platform for 20 s before being removed from the pool. On the day after completion of the spatial training, a probe trial was conducted to determine the extent to which the mice had learned to find the location of the platform. The platform was removed from the pool, and the mice were allowed to swim freely for 90 s. The number of visits to each quadrant of the maze was recorded.

Rota-Rod is a test for motor function, balance and coordination and comprises a rotating drum which is accelerated from 4 to 40 revolutions per minute over the course of 5 min. Mice were placed individually on the revolving drum (Ugo Basile, Comerio, Varese, Italy). Once they were balanced, the drum was accelerated. The time in seconds at which each animal fell from the drum was recorded using a stop-watch. Each animal received three consecutive trials, the longest time on the drum being used for analysis.

Open field: Spontaneous activity in open-field was tested in a gray Perspex arena (120 cm in diameter, 25 cm high). The animal was placed in the center of the open field and was allowed to explore it for 5 min. The behavior was recorded by a PC-linked overhead video camera. "VideoMot 2" (TSE) software was used to calculate the distance traveled and the time spent in the center, intermediate or the peripheral zones of the open field.

Prepulse inhibition (PPI): To measure the startle reactivity, mice were placed in small metal cages (90×40×40 mm) which restrict major movements and exploratory behavior. The cages are equipped with a movable platform floor attached to a sensor recording vertical movements of the floor. The cages are placed in four sound-attenuating isolation cabinets (TSE). A startle reflex is evoked by acoustic stimuli delivered from a loudspeaker suspended above the cage and connected to an acoustic generator. The startle reaction of a mouse to the acoustic stimuli evokes a movement of the platform. The transient force resulting from this movement of the platform is recorded on a personal computer during a recording window of 260 ms and stored in the computer for further evaluation. The recording window is measured from the onset of the acoustic stimuli. An experimental session consisted of a 2 min habituation to the 65 dB background white noise (continuous throughout the session), followed by a baseline recording for 1 min at background noise. After baseline recording, 6 pulse alone trials using the startle stimuli of 120 dB intensity and 40 ms duration were applied in order to decrease influence of within-session habituation. These data were not included in the analysis of the prepulse inhibition. For tests of prepulse inhibition, the 120 dB/40 ms startle pulse was applied either alone or preceded by a prepulse stimuli of 70, 75 and 80 dB intensity and 20 ms duration. An interval of 100 ms with background white noise was employed between each prepulse and pulse stimuli. The trials were presented in a pseudorandom order with an interval ranging from 8 to 22 s. Amplitude of the startle response (expressed in mV) was defined as a difference between the maximum force detected during a recording window and the force measured immediately before the stimulus onset. Amplitudes were averaged for each individual animal, separately for both types of trials (stimulus alone, stimulus preceded by a prepulse). Prepulse inhibition was calculated as a percentage of the startle response using the formula: % pulse inhibition=100−[(startle amplitude after prepulse−pulse pair)/(startle amplitude after pulse only)×100].

Statistical analysis: Data expressed as mean±SEM in figures and text were compared by analysis of variance (ANOVA) with post-hoc planned comparisons, or Kruskal-Wallis ANOVA with Mann-Whitney U-test using STATISTCA (StatSoft Inc., Tulsa, Okla., USA) software. A p-value $\leq 0.05$ was considered significant.

Figure 2:
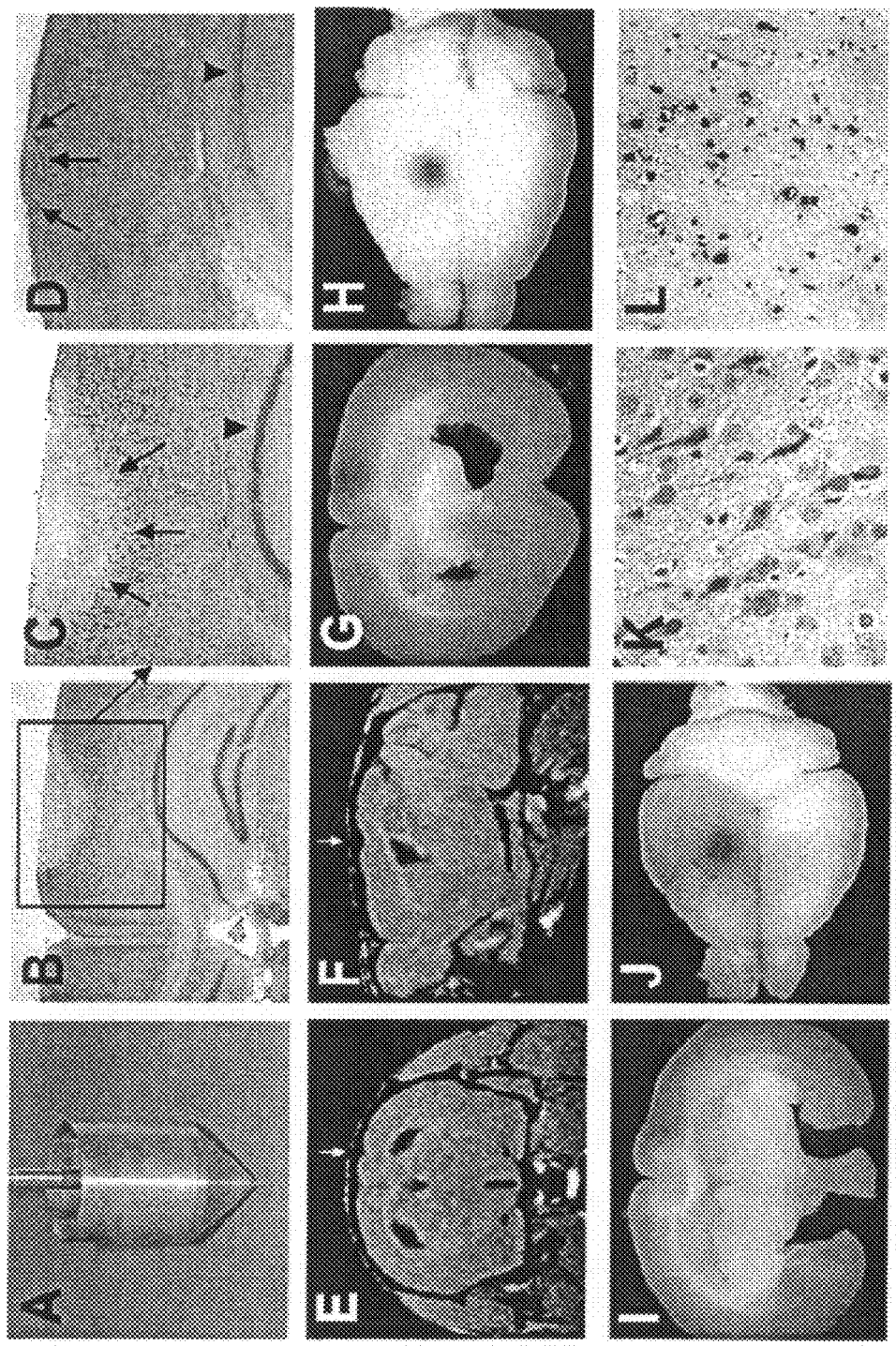
FIG. 2 shows characterization of the lesion model and evolution of the cortical lesion.

FIG. 2 shows a characterization of the lesion model and evolution of the cortical lesion. (a) Lesion maker with a tip diameter of 1 mm. (b-d) Evolution of lesion on hematoxylin-eosin stained sections, at 24 h (b,c) and 9 months (d) after lesioning (lesion depicted by arrows, hippocampal CA1 region with arrow heads). (e,f) Lesion is visible at 3 months in MRI as a small indentation on the cortical surface. (g-j) Illustration of Evans-Blue albumin leakage (as indicator of blood-brain-barrier breakdown) 30 min (g,h) and 24 h (i,j) after lesion. Ongoing apoptosis at 24 h is evident as cleaved caspase-3 (k) and TUNEL positive (l) cells surrounding the lesion.

FIG. 3 shows a ratio of cell proliferation to cell death in the dentate 24 h after unilateral cortical lesion. Many bromodeoxyuridine (BrdU) (a,a1) and few cleaved caspase-3 (b,b1) positive cells (arrows) in the contralateral dentate of an EPO-treated animal at 24 h after lesion. (c) BrdU/cleaved caspase-3 ratio calculated using bilateral dentate cell counts 24 h after lesion; n=5–7.

Figure 4:
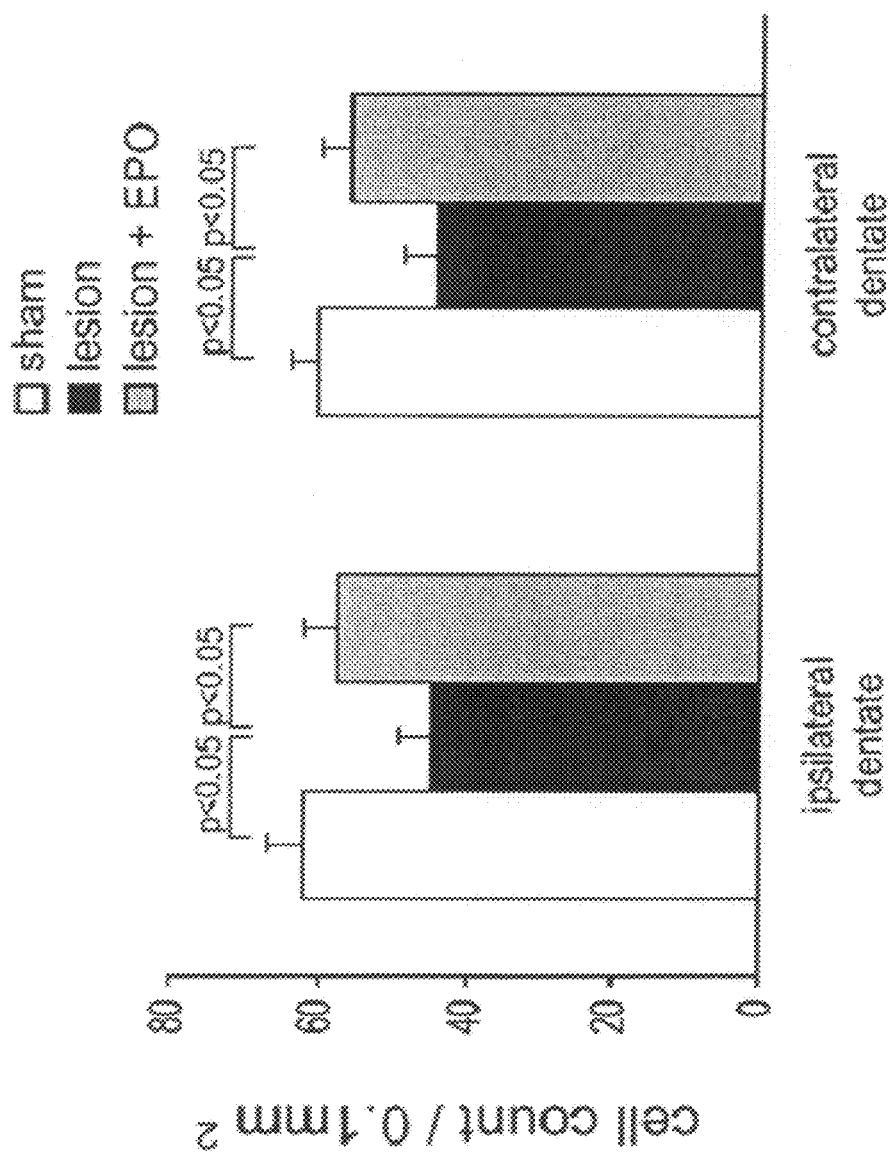
FIG. 4 shows dentate hilus cell counts 3 months after unilateral parietal cortical lesion in mice.

FIG. 4 shows dentate hilus cell counts 3 months after unilateral parietal cortical lesion in mice (n=6–7). EPO treatment prevents the lesion-induced dentate hilus cell loss. Cell counts in ipsilateral (right) and contralateral (left) dentate hilus in sham, lesion and lesion+EPO groups at 3 months.

Figure 5:
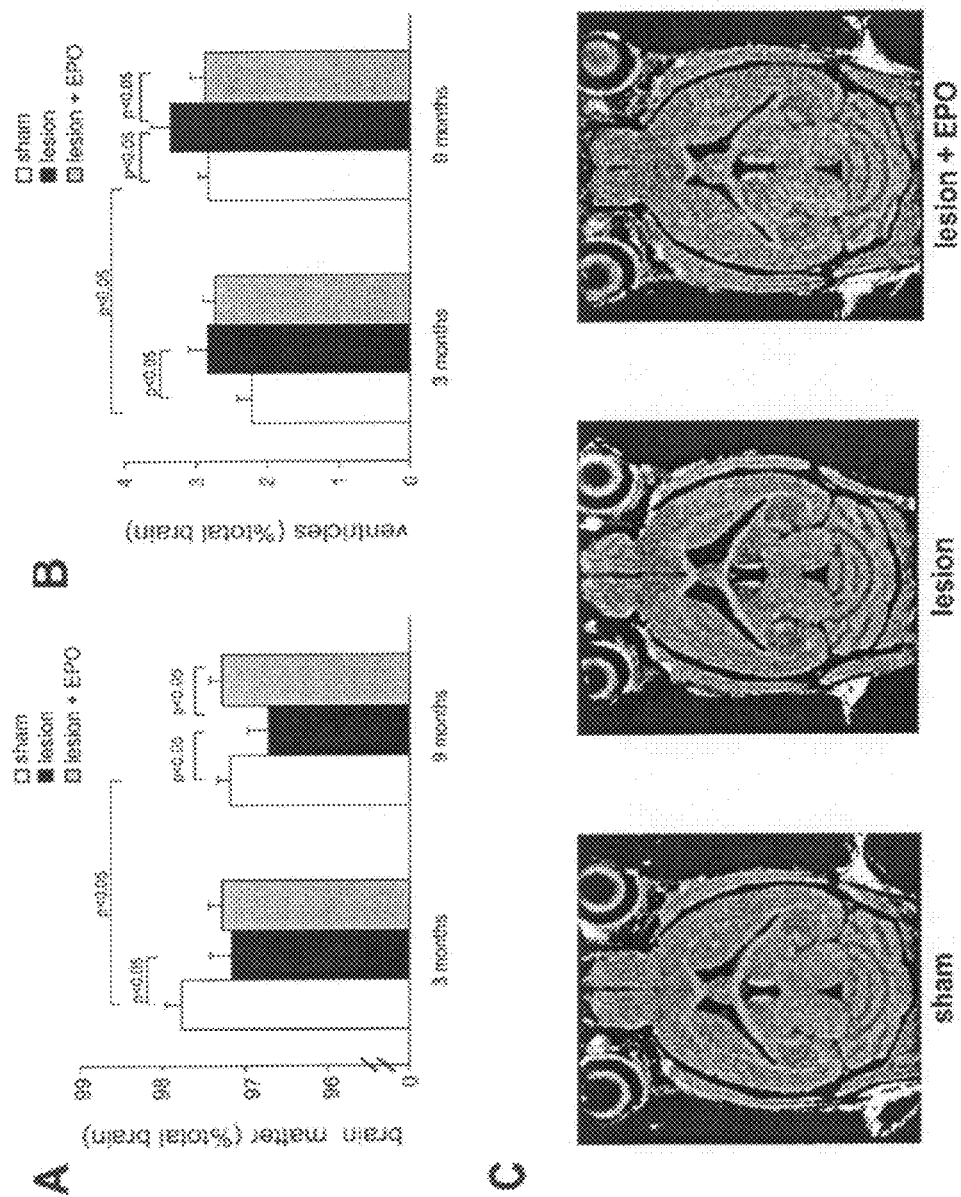
FIG. 5 shows morphological changes months after unilateral parietal cortical lesion in mice.

FIG. 5 shows morphological changes months after unilateral parietal cortical lesion in mice (n=7–12). (a) Brain matter reduction and (b) ventricular enlargement as revealed by in vivo 3D MRI at 3 and 9 months after unilateral parietal cortical lesion and their prevention by EPO. (c) Representative T1-weighted MR images (117 µm isotropic resolution) at 9 months survival time point of a sham, lesion, and lesion+EPO mouse brain demonstrating ventricular enlargement and global increase in liquor space upon lesion. These effects are prevented by early EPO treatment.

FIG. 6 shows behavioral follow-up 3 and 9 months after unilateral parietal cortical lesion in mice (n=10–19). (a,b) Performance in open field at (a) 3 months and (b) 9 months after lesion. Depicted are the time spent in the 3 three different zones of the open field (periphery, intermediate and center zones) and, as insert, the total distance traveled in sham, lesion and lesion+EPO groups. (c) Number of head dips in the hole board test and (d) percent of open arm entries in the elevated plus-maze are significantly increased in lesioned as compared to sham-operated or lesion+EPO groups.

FIG. 7 shows performance in Morris-Water-Maze 3 and 9 months after unilateral parietal cortical lesion in mice (n=10–19). Depicted in panels a and b are the latency to find the hidden platform and, as insert, the number of visits to the target site in the probe trial (platform removed) on day 9 in sham, lesion and lesion+EPO groups; *p≦0.05 lesion compared to sham, +p≦0.05 lesion compared to lesion+FEPO. Panels c and d show the latency to find the visible platform of these mice.

FIG. 8 shows behavioral follow-up three months after unilateral parietal or occipital cortical lesion in mice (n=7–13). Prepulse inhibition is attenuated in lesioned as compared to sham-operated or lesion+EPO treated groups both after parietal (a) and occipital (b) cortical lesion and, as insert, the magnitude of acustic startle without prepulse in sham, lesion and lesion+EPO groups. (c) Number of head dips in the hole board test and ventricular size in MRI are not different in the 3 groups at 3 months after occipital lesion.

Figure 9:
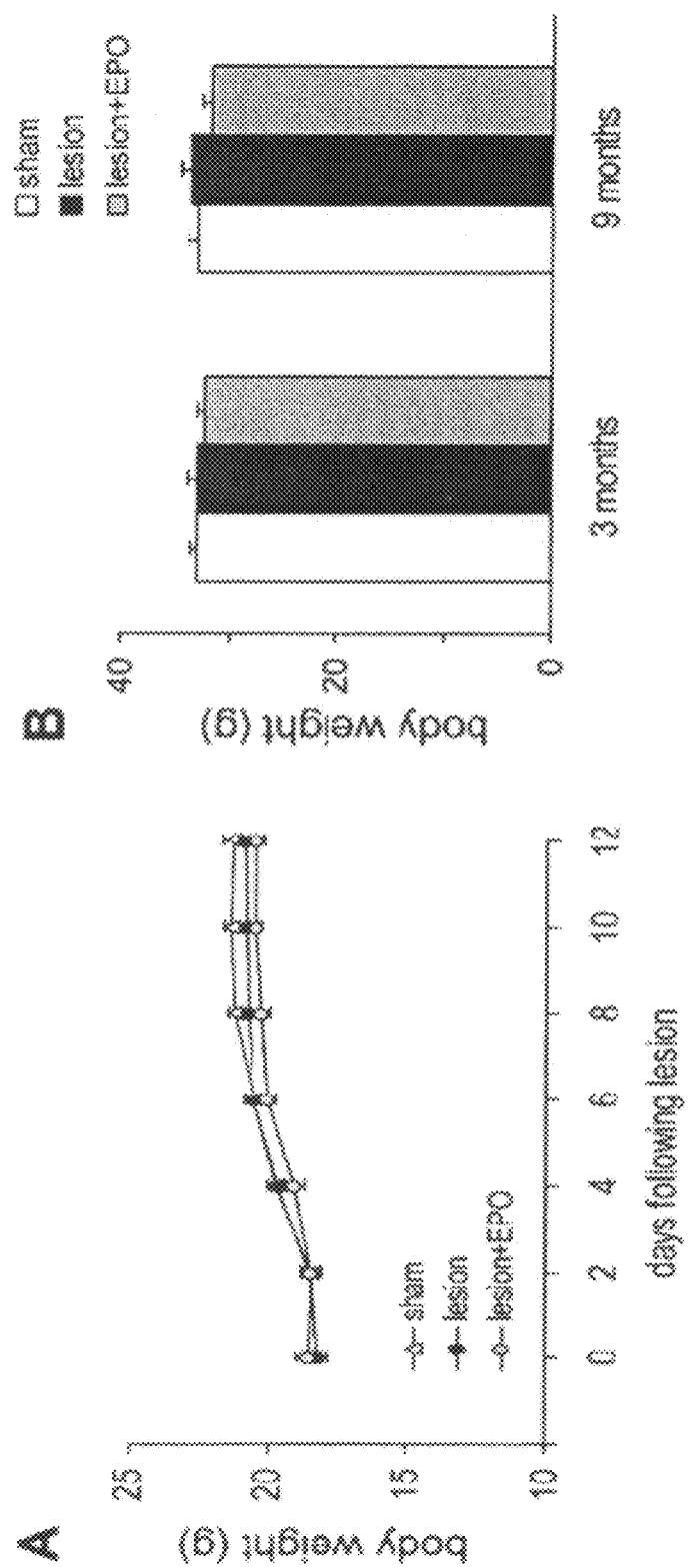
FIG. 9 shows body weight changes after unilateral parietal cortical lesion in mice.

FIG. 9 shows body weight changes after unilateral parietal cortical lesion in mice. (a) Body weight development during EPO/placebo infusions immediately following setting of the lesion (n=11). (b) Body weight 3 months and 9 months after setting the lesion (n=7–8).

Schizophrenia is increasingly recognized as a disease, characterized by a progressive degenerative component, comprising cognitive decline and loss of cortical gray matter. We hypothesized that a neuroprotective/neurotrophic add-on strategy, recombinant human erythropoietin (rhEPO) in addition to stable antipsychotic medication, may be able to improve cognitive function even in chronic schizophrenic patients. Therefore, we designed a double-blind, placebo-controlled, randomized, multicenter, proof-of-principle (phase II) study. This study had a total duration of 2 years and an individual duration of 12 weeks with an additional safety visit at 16 weeks. Chronic schizophrenic men (N=39) with defined cognitive deficit (≧1 SD below normal in the RBANS), stable medication and disease state were treated for 3 months with a weekly short (15 min) intravenous infusion of 40,000 IU rhEPO (N=20) or placebo (N=19). Main outcome measure was cognitive function (RBANS subtests delayed memory, language-semantic fluency, attention, and WCST-64-perseverative errors) tested over 2 days at baseline, 2 weeks, 4 weeks, and 12 weeks of study participation. Both, placebo and rhEPO patients improved in all evaluated categories. Patients receiving rhEPO showed a significant gradual improvement over placebo patients in schizophrenia-related cognitive functions (RBANS subtests, WCST-64), without yet reaching a plateau at 12 weeks, but no effects on psychopathology or social functioning. Also, a significant decline in serum levels of S100B, a glial damage marker, occurred upon rhEPO. The fact that rhEPO is the first compound to exert a selective and lasting beneficial effect on cognition should encourage new treatment strategies for schizophrenia.

Schizophrenia is a common and devastating disease, affecting approximately one percent of the population across cultures, mainly young people, with two thirds of them displaying severe losses of their previously acquired cognitive capacity. Among those, many fulfill the deterioration criteria of Kraepelin's dementia praecox. The disability of schizophrenic patients is a composite of persistent positive symptoms, cognitive decline, and mostly increasing negative symptoms over time, together with numerous features of general psychopathology. The therapeutic application of dopamine antagonists, i.e. antipsychotic drugs, mainly addresses the "tip of the iceberg", leading to a level of outside normality in these patients, that enables them and their environment, to cope with the disease. With the newer generation of antipsychotics and their fewer side effects regarding extrapyramidal motor signs, patients' compliance, an essential factor for longterm prognosis, seemed to improve. This improvement, however, has been questioned recently, as has the ability of these drugs to improve cognitive functioning. Unfortunately, no drug up to now has been clearly shown to have lasting beneficial effects on cognition in schizophrenia.

The increasing knowledge about neurodegenerative mechanisms acting in schizophrenia, particularly that derived from imaging data demonstrating progressive loss of cortical gray matter in this condition, have led to a virtual renaissance of Kraepelin's dementia praecox considerations, and have stimulated novel concepts of the disease, including therapeutic neuroprotection. Based on previous observations by ourselves and others, erythropoietin (EPO) appears to be a promising candidate for neuroprotection in schizophrenia. EPO can be expected to address some of the pathophysiological mechanisms presumably involved in the progression of schizophrenic psychosis. In particular, it exerts neurotrophic and synaptogenic activity. Encouraging results about its neuroprotective/neurotrophic power in man have been obtained from our recent treatment trial in stroke patients. In previous work, we have shown by using nuclear imaging technology in man that peripherally applied recombinant human (rh) EPO penetrates into the brain. Moreover, we demonstrated that rhEPO is enriched intracranially, and notably more in schizophrenic patients than in healthy controls. In line with reactive EPO receptor expression in the brain upon metabolic distress, we found EPO receptors densely expressed in hippocampus and cortex of schizophrenic subjects but not of healthy individuals. Most importantly, we demonstrated in a murine lesion model of progressive neurodegeneration, resembling features of schizophrenia, that longterm behavioral alterations as well as brain atrophy could be prevented by rhEPO. These observations, together with the known safety of rhEPO, let us initiate the present proof-of-principle trial exploring whether a neuroprotective add-on strategy (rhEPO in addition to stable antipsychotic medication) in schizophrenia that targets cognition may be a promising novel approach to treatment of the disease.

Although first episode schizophrenic patients with their progressing cognitive deterioration would certainly have been the population of choice for the present double-blind placebo-controlled randomized multicenter trial, we took the risk to focus on chronically ill, cognitively impaired schizophrenic patients. We did this due to ethical considerations (longterm compliance, informed consent, legal situation in a first proof-of-principle trial) but, most importantly, under the assumption that any brain has potential to recover, with processes of degeneration and regeneration constantly running in parallel. Here we show that a neuroprotective growth factor, rhEPO, which possesses properties to slow down degeneration and to amplify regeneration, can indeed improve cognitive functioning in schizophrenia.

Of the patients completing the study (N=39), most were included by the centers in Göttingen (N=17) and Kiel (N=14), fewer patients by Homburg (N=4), Cologne (N=3) and Marburg (N=1). Despite this unequal distribution of patients among centers, there was no indication of a center effect with respect to study results (see below).

Of 172 patients screened for participation in the study, only 43 fulfilled the enrolment criteria. The most common reasons for exclusion were duration of disease less than 10 years, last acute episode less than 6 months ago, unstable medication, unwillingness to participate in a trial, PANSS scoring outside the requested limits.

No unexpected side effects, no adverse events and no complaints of the participating patients were identified throughout the study. A total of 8 patients reached the criteria for blood letting (hematocrit ≧50 on 2 consecutive measurements): 5 patients had to be bled (350-450 ml) once, 1 patient twice, 1 patient 3 times, 1 patient 5 times. All bleedings were well tolerated.

Baseline characteristics of patients completing the study are presented in Table 1. EPO and placebo group turned out to match well with respect to sociodemographic parameters as well as disease history. Also, there was no significant difference between groups regarding antipsychotic medication (type of antipsychotic; chlorpromazine equivalents, determined according to), additional use of anticholinergic drugs, benzodiazepines, or smoking habits (Table 2).

Psychopathological data are presented in Table 3. Upon inclusion, groups did not differ significantly with respect to PANSS scales, subjective well-being, or DAS-M. PANSS negative and general psychopathology scales improved over time in both treatment groups but did not show an interaction effect between group and time (Table 3).

Figure 12:
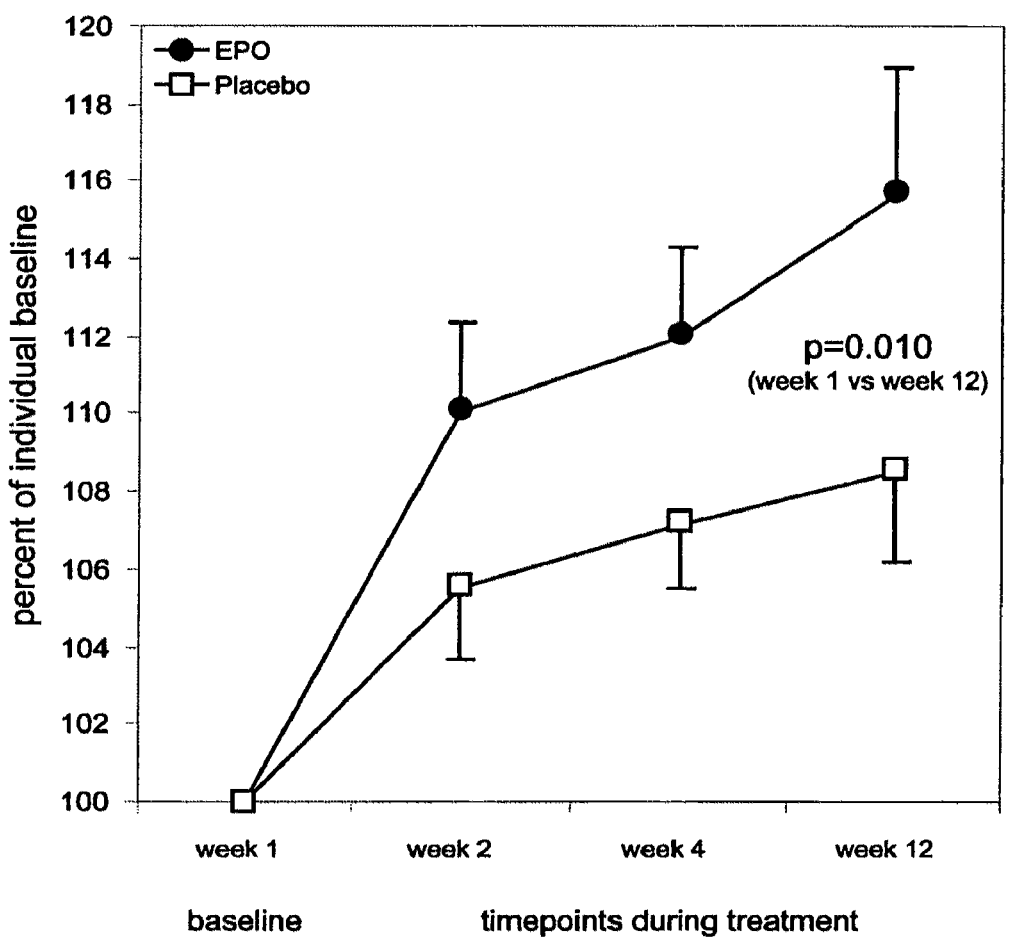
FIG. 12 shows repeated measures analysis of covariance: Effect of erythropoietin (N=19) versus placebo (N=19) treatment on cognitive parameters in male chronic schizophrenic patients.

The composite score of the set of schizophrenia-related cognitive tests (RBANS subtests delayed memory, language-semantic fluency, attention, and WCST-64-perseverative errors) also did not differ between treatment groups upon inclusion (EPO: Mean=−0.93, SD=4.89; Placebo: Mean=1.47, SD=3.95; df=36, ns). Interestingly, both groups gradually improved in cognitive functions over all timepoints (EPO: p=0.0001, df=18; placebo: p=0.0022, df=18) (FIG. 12). Repeated measures analysis of covariance (repeated measures ANCOVA) using this composite score as the dependent variable and treatment as the independent variable, together with age as covariate, revealed a significantly better outcome of EPO as compared to placebo treated patients. This result was obtained both by using raw data (p=0.022, df=1, 35) and by calculating cognitive improvement based on the individual baseline level (p=0.010, df=1, 35) (FIG. 12).

Cognitive tests other than those selected as "schizophrenia test set", and motor tests did not differ between groups upon inclusion or during follow-up (Table 4). Also, single test analysis over time (in contrast to the composite score) did not yield significant differences between groups. In both groups, however, data improved over the study period, in particular initially, consistent with a drug-independent trial effect (Table 4).

TABLE 1

| Patient characteristic | | | |
|---|---|---|---|
| | Patients - EPO N = 20 M (± s.d.) | Patients - Placebo N = 19 M (± s.d.) | Significant (t-test) P-value |
| Age (years) | 39.6 (7.4) | 43.0 (6.1) | NS 0.122 |
| Duration of disease | 16.3 (7.8) | 18.5 (5.5) | NS 0.312 |
| Years of education | 12.2 (3.4) | 12.8 (3.3) | NS 0.557 |
| MWT-B (raw data; scale range 0-37) (premorbid intelligence estimate | 27.3 (8.5) | 29.5 (5.3) | NS 0.326 |
| | Patients - EPO N = 20 Number (%) | Patients - placebo N =19 Number (%) | Significant ($X^2$-test) P-value |
| Unemployed | 8 (42.1%) | 10 (50.0%) | NS 0.621 |
| Partnership living alone | 20 (100%) | 17 (89.5%) | NS 0.136 |
| Children | 3 (15.0%) | 3 (15.8%) | NS 1.000 |

Abbreviations: EPO, erythropoietin; M, mean; MWT-B, Mehrfachwahl-VVortschatz-Intelligenztest; NS, nonsignificant

TABLE 2

| Stable baseline medication | | | |
|---|---|---|---|
| | Patients - EPO N = 20 M (± s.d.) | Patients - Placebo N = 19 M (± s.d.) | Significant (t-test) P-value |
| Chlorpromazine equivalents | 493.8 (355.5) | 413.3 (424.3) | NS 0.524 |
| | Patients - EPO N = 20 Number (%) | Patients - placebo N = 19 Number (%) | Significant ($X^2$-test) P-value |
| Antipsychotic medication typical:atypical:combination | 3 (15%):10 (50%):7 (35%) | 7 (36.8%):9 (47.4%):3 (15.8) | NS 0.199 |
| Anticholinergic drugs | 3 (15%) | 4 (21.7%) | NS 0.622 |
| Patients with benzodiazepines | 7 (35.0%) | 5 (26.3%) | NS 0.731 |
| Cigarette smoking non-smoker:smoker:ex-smoker | 4 (20.0%):15 (75.0%):1 (5.0%) | 3 (15.8%):13 (68.4%):3 (15.8%) | NS 0.532 |

Abbreviations: EPO, erythropoietin; M, mean; NS, nonsignificant

TABLE 3

| Psychopathological data (N = 16-20, due to missing data | | | | | | |
|---|---|---|---|---|---|---|
| | Week 1 M (± s.d.) - baseline | Week 2 M (± s.d.) | Week 4 M (± s.d.) | Week 8 M (± s.d.) | Week 12 M (± s.d.) | Time (week 1-week 12) Time (week 1-week 12) by group, P-value |
| PANSS Positive Scale (scale range 7-49) | | | | | | |
| EPO (N = 19-20) | 14.1 (3.7) | 16.2 (5.4) | 16.0 (5.2) | 14.3 (3.7) | 14.7 (4.6) | 0.597 |
| Placebo (N = 18-19) | 15.0 (4.1) | 15.5 (4.0) | 15.2 (3.2) | 14.8 (4.0) | 13.6 (3.4) | 0.156 ) d.f. = 1, 36)[a] |

TABLE 3-continued

Psychopathological data (N = 16-20, due to missing data)

| | Week 1 M (± s.d.) - baseline | Week 2 M (± s.d.) | Week 4 M (± s.d.) | Week 8 M (± s.d.) | Week 12 M (± s.d.) | Time (week 1-week 12) Time (week 1-week 12) by group, P-value |
|---|---|---|---|---|---|---|
| PANSS Negative Scale (scale range 7-49) | | | | | | |
| EPO (N = 20) | 29.8 (5.6) | 27.8 (5.3) | 26.6 (5.1) | 24.4 (6.1) | 26.2 (5.9) | <0.001 |
| Placebo (N = 18-19) | 26.5 (5.8) | 24.9 (4.6) | 23.7 (4.7) | 23.9 (5.0) | 22.1 (5.6) | .0638 d.f. = 1, 37[a] |
| PANSS General Scale (scale range 16-112) | | | | | | |
| EPO (N = 20) | 53.4 (10.5) | 48.9 (8.9) | 47.5 (9.3) | 42.1 (6.9) | 44.9 (9.9) | <0.001 |
| Placebo (N = 18-19) | 48.6 (6.7) | 46.2 (6.8) | 44.7 (7.1) | 43.1 (7.5) | 38.8 (8.8) | 0.682 (d.f. = 1, 37)[a] |
| Subjective well-being(scale range 20-120) | | | | | | |
| EPO (N = 17-20) | 77.5 (14.0) | 81.9 (14.7) | 81.0 (12.2) | — | 81.2 (12.0) | 0.027 |
| Placebo (N = 17-19) | 83.9 (16.3) | 82.6 (12.6) | 84.4 (12.8) | — | 87.9 (15.4) | 0.969 (d.f. = 1, 35)[a] |
| DAS-M (scale range 0-5) | | | | | | |
| EPO (N = 17-20) | 3.2 (0.7) | 3.2 (0.6) | 3.2 (0.6) | — | 3.0 (0.7) | 0.161 |
| Placebo (N = 16-18) | 3.1 (1.0) | 3.1 (1.0) | 3.1 (1.0) | — | 3.2 (0.6) | 0.458 (d.f. = 1, 34)[a] |

Abbreviations: DAS-M, disability assessment schedule; EPO, erythropoietin; M, mean; PANSS, Positive and Negative Syndrome Scale
[a] Degrees of freedom (d.f.) are identical for time and time by group.

Volumetrical analysis of whole brain MRI data did not reveal significant differences between groups nor changes following treatment (total volume upon inclusion 1549.9±108.8 ml versus 1474.6±154.4 ml and after 12 weeks of treatment 1547.9±106.0 ml versus 1468.3±153.0 ml in EPO (n=16) versus placebo (n=12) patients, respectively).

Routine laboratory data over the course of the trial are presented in Table 5, with significant differences between the groups marked in gray. Remarkable differences over time occurred particularly with erythrocytes, reticulocytes, hemoglobin, hematocrit, mean corpuscular hemoglobin (MCH), transferrin, and ferritin.

EPO levels did not differ among groups upon inclusion and remained in the same range over the whole study period, independent of treatment (Table 6). Hepcidin prohormone, a recently discovered hepatic peptide that regulates intestinal iron absorption, was found unaffected by EPO treatment as was the inflammatory cytokine IL-6, which had previously been found to be elevated in schizophrenia (Table 6). Both hepcidin and IL-6 did not differ significantly between groups and were always within the normal range (according to manufacturers).

Figure 13:
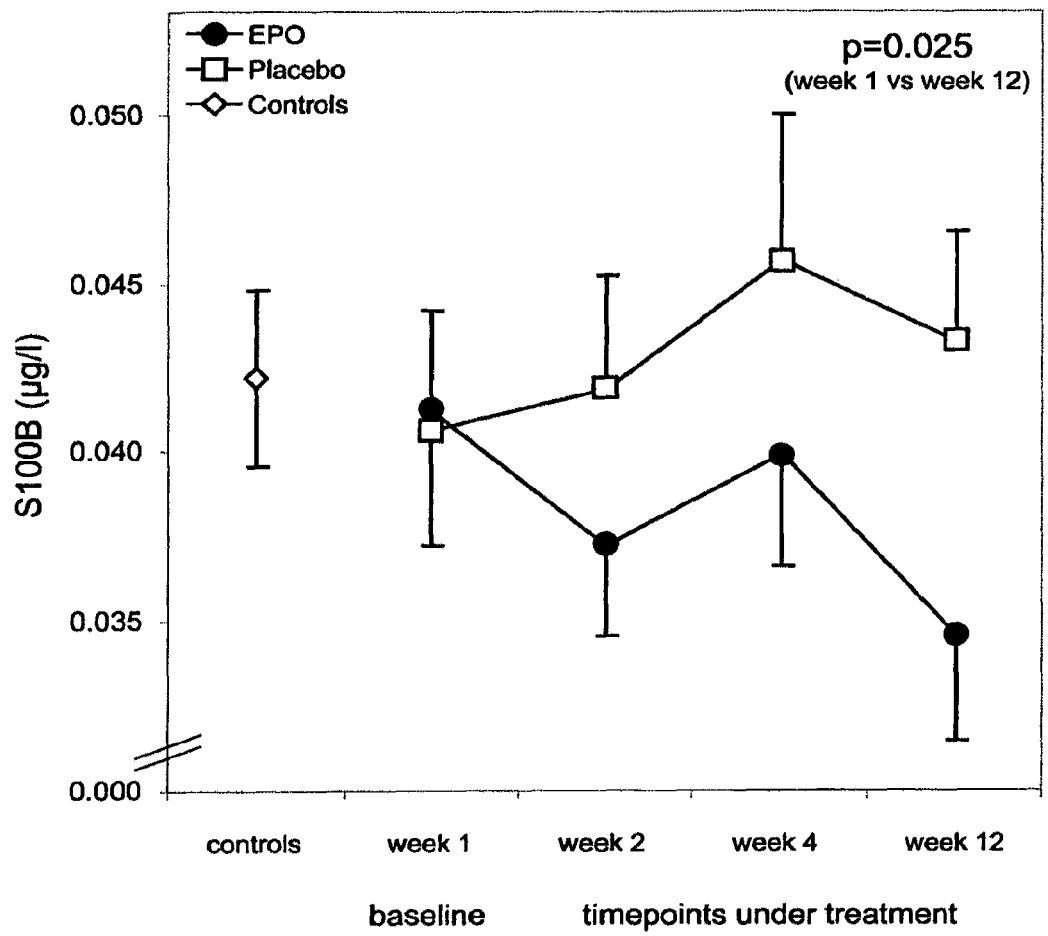
FIG. 13 shows repeated measures analysis of covariance: Effect of erythropoietin (N=15) versus placebo (N=15) treatment on S100B serum levels in male chronic schizophrenic patients.

In contrast, serum levels of the glial damage marker S100B, starting out from almost identical baseline concentrations in both groups (that did not differ from age-matched healthy men; n=27), dissociated remarkably upon treatment, with the EPO group showing a significant decrease at week 12 (p=0.025, df=1, 27) (FIG. 13). Repeated measures ANCOVA, using S100B as the dependent variable, treatment as the independent variable, and age as a covariate, did not identify further covariates of significant influence on this result (premorbid intelligence (MWT-B), duration of disease, baseline cognitive performance, PANSS negative or general psychopathology symptoms, chlorpromazine equivalents, hematologic parameters including blood letting, creatinine, body weight or height).

Similarly, the only covariate identified to be of significant influence on cognitive outcome was age. Specifically, there was no additional effect of S100B at week 12 or upon inclusion, medication, duration of disease, premorbid intelligence (MWT-B), baseline PANSS negative, positive, or general psychopathology scores. Careful and comprehensive analysis of hematologic parameters, as altered by continuous high dose rhEPO treatment, including delta values, with respect to a potential influence on cognitive outcome did not show significant effects.

When data obtained in Gottingen (9 EPO, 8 placebo patients), in Kiel (7 EPO, 7 placebo patients), and in the remaining 3 centers (4 EPO, 4 placebo patients) were analyzed separately, they all resulted in the same pattern, with the EPO group superior to the placebo group. This finding excluded a major center bias explaining the result. Due to the small number of patients in these separate analyses, however, this statistical manoeuvre did not yield significant differences anymore.

TABLE 4

Cognitive raw data immediately before the first EPO/placebo infusion (week 1) and at three times points during treatment (N = 19-20, due to missing data at baseline of only one particular patient. For repeated-measures ANCOVA, this one patient has been excluded from the analysis resulting in N = 19 patients per group - compare FIG. 3)

| | Week 1 M (± s.d.) - baseline | Week 2 M (± s.d.) | Week 4 M (± s.d.) | Week 12 M (± s.d.) | Time (week 1-week 12) Time (week 1-week 12) by group, P-value |
|---|---|---|---|---|---|
| RBANS language-semantic fluency (scale range 0-38+) | | | | | |
| EPO (N = 20) | 13.5 (4.0) | 17.4 (5.2) | 14.7 (3.9) | 17.3 (4.0) | <0.001 |
| Placebo (N = 19) | 16.9 (5.2) | 19.4 (6.9) | 18.1 (4.3) | 19.9 (5.0) | 0.658 (d.f. = 1, 37)[a] |

TABLE 4-continued

Cognitive raw data immediately before the first EPO/placebo infusion (week 1) and at three times points during treatment (N = 19-20, due to missing data at baseline of only one particular patient. For repeated-measures ANCOVA, this one patient has been excluded from the analysis resulting in N = 19 patients per group - compare FIG. 3)

| | Week 1 M (± s.d.) - baseline | Week 2 M (± s.d.) | Week 4 M (± s.d.) | Week 12 M (± s.d.) | Time (week 1-week 12) Time (week 1-week 12) by group, P-value |
|---|---|---|---|---|---|
| *RBANS attention-digit span (scale range 0-16)* | | | | | |
| EPO (N = 20) | 8.4 (2.2) | 8.9 (2.3) | 9.2 (2.1) | 9.7 (2.3) | 0.047 |
| Placebo (N = 19) | 9.1 (2.1) | 9.7 (2.4) | 9.8 (2.6) | 9.2 (2.2) | 0.088 (d.f. = 1, 37)[a] |
| *RBANS attention-coding (scale range 0-89)* | | | | | |
| EPO (N = 20) | 34.6 (11.2) | 36.9 (12.6) | 36.5 (13.4) | 38.9 (11.7) | <0.001 |
| Placebo (N=19) | 36.0 (8.7) | 36.2 (9.9) | 36.0 (9.4) | 36.9 (8.5) | 0.174 (d.f. = 1, 37)[a] |
| *RBANS delayed memory-list recognition (scale range 0-20)* | | | | | |
| EPO (N = 20) | 18.8 (1.8) | 18.9 (1.4) | 19.2 (1.0) | 19.0 (1.2) | 0.589 |
| Placebo (N-19) | 19.6 (0.6) | 19.2 (1.2) | 19.5 (0.8) | 19.2 (0.8) | 0.258 (d.f. = 1, 37)[a] |
| *RBANS delayed memory-list recall (scale range 0-10)* | | | | | |
| EPO (N = 20) | 4.8 (3.0) | 5.7 (2.5) | 5.4 (2.3) | 6.5 (2.6) | <0.001 |
| Placebo (N-19) | 5.4 (2.3) | 6.7 (2.1) | 6.1 (2.3) | 7.3 (1.9) | 0.725 (d.f. = 1, 37)[a] |
| *RBANS delayed memory-story recall (scale range 0-12)* | | | | | |
| EPO (N = 20) | 6.2 (3.0) | 7.2 (3.0) | 8.4 (2.5) | 7.5 (3.1) | 0.025 |
| Placebo (N = 19) | 7.3 (2.7) | 7.5 (2.7) | 8.5 (2.8) | 8.3 (3.3) | 0.762 (d.f. = 1, 37)[a] |
| *RBANS delayed memory-figure recall (scale range 0-20)* | | | | | |
| EPO (N = 20) | 10.1 (5.4) | 12.9 (4.8) | 13.7 (4.5) | 13.7 (5.2) | <0.001 |
| Placebo (N = 19) | 11.4 (3.6) | 13.0 (3.4) | 13.2 (3.9) | 12.9 (3.2) | 0.079 (d.f. = 1, 37)[a] |
| *WCST perseverative errors (scale range 0-63)* | | | | | |
| EPO (N = 20) | 13.7 (9.5) | 13.4 (9.2) | 10.2 (7.0) | 9.5 (5.6) | <0.001 |
| Placebo (N = 19) | 11.9 (7.1) | 9.4 (6.1) | 9.5 (7.6) | 8.0 (6.4) | 0.676 (d.f. = 1, 36)[a] |
| *RBANS immediate memory-list learning (scale range 0-40)* | | | | | |
| EPO (N = 20) | 24.7 (5.7) | 27.4 (6.0) | 27.4 (7.4) | 28.2 (6.8) | <0.001 |
| Placebo (N-19) | 25.5 (4.7) | 27.5 (6.1) | 28.6 (4.3) | 30.5 (4.7) | 0.332 (d.f. = 1, 37)[a] |
| *RBANS immediate memory-story memory (scale range 0-24)* | | | | | |
| EPO (N = 20) | 13.6 (4.2) | 14.3 (4.7) | 16.0 (3.6) | 15.0 (4.7) | <0.022 |
| Placebo (N-19) | 13.5 (3.9) | 14.3 (5.1) | 15.9 (4.8) | 16.4 (4.2) | 0.445 (d.f. = 1, 37)[a] |
| *RBANS visuospatial-figure copy (scale range 0-20)* | | | | | |
| EPO (N = 20) | 16.9 (2.3) | 17.7 (1.6) | 17.3 (2.4) | 7.8 (1.4) | 0.013 |
| Placebo (N = 19) | 16.7 (1.9) | 17.4 (1.9) | 16.9 (1.6) | 17.4 (1.7) | 0.743 (d.f. = 1, 37)[a] |
| *RBANS visuospatial-line orientation (scale range 0-20)* | | | | | |
| EPO (N = 20) | 15.6 (4.2) | 16.4 (3.5) | 17.0 (3.8) | 16.7 (3.0) | <0.149 |
| Placebo (N = 19) | 16.7 (3.1) | 16.9 (3.0) | 17.7 (3.0) | 17.4 (3.3) | 0.716 (d.f. = 1, 37)[a] |
| *RBANS language-picture naming (scale range 0-10)* | | | | | |
| EPO (N = 20) | 10.0 (0.2) | 10.0 (0.2) | 10.0 (0.0) | 10.0 (0.0) | <0.083 |
| Placebo (N = 19) | 9.9 (0.3) | 10.0 (0.0) | 9.9 (0.2) | 10.0 (0.0) | 0.530 (d.f. = 1, 37)[a] |
| *Dotting (scale range 0-100)* | | | | | |
| EPO (N = 20) | 36.3 (12.6) | 39.7 (11.4) | 42.8 (13.7) | 42.3 (12.9) | <0.001 |
| Placebo (N-19) | 42.9 (11.3) | 47.1 (13.2) | 49.7 (12.6) | 48.8 (12.2) | 0.911 (d.f. = 1, 36)[a] |
| *Tapping (scale range 0-70)* | | | | | |
| EPO (N = 20) | 26.5 (8.1) | 27.7 (7.3) | 26.8 (8.2) | 29.5 (9.1) | <0.001 |
| Placebo (N-19) | 27.2 (8.7) | 30.7 (10.1) | 31.3 (8.8) | 32.2 (10.7) | 0.278 (d.f. = 1, 36)[a] |

Abbreviations: EPO, erythropoietin; M, mean; RBANS, Repeatable Battery for the Assessment of Neuropsychological Status; WCST, Wisconsin Card Sorting Test.
[a]Degrees of freedom (d.f.) are identical for time and time by group.

TABLE 5

Routine laboratory data (N = 15-20, due to missing data; significant differences by f-test are marked in gray)

|  | Week 1 M (± s.d.) - baseline | Week 2 M (± s.d.) | Week 3 M (± s.d.) | Week 4 M (± s.d.) | Week 5 M (± s.d.) | Week 6 M (± s.d.) | Week 7 M (± s.d.) |
|---|---|---|---|---|---|---|---|
| Erythrocytes (mia/pt) | | | | | | | |
| EPO | 4.96 | 5.01 | 5.13 | 5.27 | 5.34 | 5.35 | 5.43 |
| (N = 19-20) | (0.46) | (0.44) | (0.46) | (0.52) | (0.49) | (0.43) | (0.48) |
| Placebo | 5.01 | 4.98 | 4.91 | 4.94 | 4.91 | 4.93 | 4.90 |
| (N = 18-19) | (0.36) | (0.31) | (0.28) | (0.33) | (0.33) | (0.32) | (0.33) |
| Reticulocytes (%) | | | | | | | |
| EPO | 10.91 | 19.17 | 17.08 | 15.89 | 13.79 | 13.84 | 13.09 |
| (N = 19-20) | (4.86) | (6.88) | (7.70) | (7.13) | 7.56 | (7.70) | (7.10) |
| Placebo | 10.97 | 11.06 | 11.21 | 11.65 | 11.71 | 11.70 | 11.39 |
| (N = 16-18) | (2.89) | (3.05) | (2.95) | (3.00) | (2.84) | (3.34) | (3.38) |
| Hemoglobin (mmol/l) | | | | | | | |
| EPO | 9.27 | 9.32 | 9.55 | 9.79 | 9.88 | 9.59 | 9.98 |
| (N = 19-20) | (0.83) | (0.83) | (0.77) | (0.95) | (0.92) | (0.83) | (0.95) |
| Placebo | 9.47 | 9.39 | 9.35 | 9.34 | 9.34 | 9.354 | 9.29 |
| (N = 18-19) | (0.70) | (0.62) | (0.59) | (0.65) | (0.75) | (0.70) | (0.62) |
| Hematocrit (%) | | | | | | | |
| EPO | 44.46 | 44.54 | 45.89 | 47.81 | 47.76 | 48.04 | 48.32 |
| (N = 19-20 | (3.88) | (3.27) | (2.97) | (4.35) | (3.86) | (3.38) | (3.91) |
| Placebo | 44.40 | 44.02 | 43.67 | 43.65 | 43.69 | 43.66 | 43.43 |
| (N = 18-19 | (3.45) | (3.01) | (2.64) | (3.36) | (3.22) | (3.26) | (3.23) |
| MCH (fl) | | | | | | | |
| EPO | 30.03 | 30.06 | 30.05 | 29.95 | 29.91 | 29.82 | 29.73 |
| (N = 19-20) | (1.70) | (1.45) | (1.53) | (1.42) | (1.60) | (1.69) | (1.84) |
| Placebo | 30.53 | 30.34 | 30.67 | 30.67 | 30.66 | 30.57 | 30.66 |
| (N = 18-19 | (1.40) | (1.39) | (1.36) | (1.76) | (1.31) | (1.37) | (1.37) |

|  | Week 6 M (± s.d.) - baseline | Week 9 M (± s.d.) | Week 10 M (± s.d.) | Week 11 M (± s.d.) | Week 12 M (± s.d.) | Week 16 M (± s.d.) | Time (week 1-week 12) Time (week 1-week 12) by group P = value |
|---|---|---|---|---|---|---|---|
| Erythrocytes (mia/pt) | | | | | | | |
| EPO | 5.49 | 5.53 | 5.49 | 5.58 | 5.71 | 5.76 | <0.001 |
| (N = 19-20) | (0.44) | (0.45) | (0.45) | (0.39) | (0.47) | (0.37) | <0.001 (d.f. = 1.37)[a] |
| Placebo | 4.88 | 4.93 | 4.93 | 4.88 | 4.97 | 5.09 | |
| (N = 18-19) | (0.33) | (0.28) | (0.28) | (0.29) | (0.29) | (0.28) | |
| Reticulocytes (%) | | | | | | | |
| EPO | 10.01 | 10.96 | 9.44 | 8.75 | 10.79 | 4.85 | 0.339 |
| (N = 15-17) | (4.14) | (5.76) | (4.54) | (4.27) | (4.66) | (2.91) | 0.253 (d.f. = 1, 37)[a] |
| Placebo | 11.84 | 11.49 | 11.99 | 11.45 | 12.33 | 11.31 | |
| (N = 16-18) | (2.51) | (4.04) | (4.65) | (3.34) | (3.92) | (3.43) | |
| Hemoglobin (mmol) | | | | | | | |
| EPO | 9.95 | 9.99 | 9.82 | 9.64 | 9.96 | 9.85 | 0.003 |
| (N = 19-20) | (0.91) | (0.85) | (0.85) | (0.71) | (0.83) | (0.44) | <0.001 (d.f. = 1, 37)[a] |
| Placebo | 9.29 | 9.34 | 9.28 | 9.21 | 9.39 | 9.55 | |
| (N = 18-19) | (0.59) | (0.52) | (0.50) | (0.59) | (0.58) | (0.69) | |
| MCH (pg) | | | | | | | |
| EPO | 48.67 | 48.74 | 48.04 | 48.43 | 49.29 | 47.81 | <0.001 |
| (N = 19-20) | (3.69) | (3.73) | (3.26) | (2.72) | (3.62) | (2.41) | <0.001 (d.f. = 1, 37)[a] |
| Placebo | 43.17 | 43.61 | 43.61 | 43.27 | 44.06 | 45.17 | |
| (N = 18-19) | (3.19) | (2.71) | (2.75) | (2.87) | (2.90) | (3.45) | |

|  | Week 1 M (± s.d.) - baseline | Week 2 M (± s.d.) | Week 3 M (± s.d.) | Week 4 M (± s.d.) | Week 5 M (± s.d.) | Week 6 M (± s.d.) | Week 7 M (± s.d.) |
|---|---|---|---|---|---|---|---|
| MCV (fl) | | | | | | | |
| EPO | 89.50 | 89.05 | 89.74 | 90.70 | 89.84 | 89.75 | 89.45 |
| (N = 19-20) | (5.27) | (3.69) | (4.59) | (4.45) | (4.40) | (3.92) | (4.88) |
| Placebo | 88.63 | 88.37 | 88.72 | 88.53 | 88.95 | 88.42 | 88.63 |
| (N = 18-19) | (2.93) | (2.95) | (3.49) | (3.29) | (3.32) | (3.29) | (3.00) |

TABLE 5-continued

Routine laboratory data (N = 15-20, due to missing data; significant differences by f-test are marked in gray)

| | | | | | | | |
|---|---|---|---|---|---|---|---|
| Thrombocytes (Tsd/µl) | | | | | | | |
| EPO | 254.00 | 249.15 | 255.58 | 254.00 | 265.74 | 275.85 | 279.25 |
| (N = 19-20) | (64.50) | (73.36) | (61.38) | (77.62) | (75.88) | (78.27) | (80.15) |
| Placebo | 243.58 | 243.37 | 245.94 | 246.68 | 248.58 | 247.53 | 248.63 |
| (N = 18-19) | (42.61) | (39.93) | (41.21) | (41.16) | (42.28) | (42.43) | (47.45) |
| Iron (µmol/l) | | | | | | | |
| EPO | 18.98 | 13.12 | 18.32 | 17.43 | 15.80 | 15.25 | 14.85 |
| (N = 19-20) | (8.91) | (3.62) | (7.66) | (8.37) | (8.56) | (7.73) | (10.05) |
| Placebo | 17.89 | 15.44 | 15.13 | 13.57 | 16.01 | 15.72 | 14.16 |
| (N = 16-19) | (7.28) | (5.68) | (5.36) | (5.35) | (7.31) | (6.70) | (5.90) |
| Transferrin (µmol/l) | | | | | | | |
| EPO | 30.63 | 30.56 | 34.03 | 33.23 | 34.03 | 34.62 | 34.19 |
| (N = 19-20) | (4.56) | (4.72) | (9.78) | (4.65) | (5.58) | (5.00) | (4.94) |
| Placebo | 28.30 | 27.84 | 28.24 | 28.44 | 28.75 | 29.39 | 28.12 |
| (N = 17-19) | (5.35) | (4.39) | (5.07) | (5.12) | (4.88) | (5.47) | (4.94) |
| Transferrin saturation (%) | | | | | | | |
| EPO | 28.70 | 19.80 | 26.27 | 24.30 | 23.23 | 20.17 | 20.15 |
| (N = 19-20) | (16.79) | (6.66) | (14.47) | (13.87) | (13.67) | (10.59) | (14.52) |
| Placebo | 29.05 | 25.66 | 25.26 | 22.24 | 26.08 | 25.72 | 24.08 |
| (N = 16-19) | (12.60) | (10.74) | (11.45) | (10.37) | (14.27) | (14.48) | (13.86) |

| | Week 6 M (± s.d.) - baseline | Week 9 M (± s.d.) | Week 10 M (± s.d.) | Week 11 M (± s.d.) | Week 12 M (± s.d.) | Week 16 M (± s.d.) | Time (week 1-week 12) Time (week 1-week 12) by group P = value |
|---|---|---|---|---|---|---|---|
| MCV(fl) | | | | | | | |
| EPO | 88.80 | 88.47 | 87.58 | 86.95 | 86.40 | 83.11 | <0.001 |
| (N = 19-20) | (4.62) | (4.39) | (4.41) | (4.24) | (4.62) | (3.61) | <0.001 (d.f. = 1, 37)[a] |
| Placebo | 88.47 | 88.74 | 88.58 | 88.42 | 88.53 | 88.63 | |
| (N = 18-19) | (2.69) | (2.75) | (3.19) | (3.29) | (2.55) | (3.55) | |
| Thrombocytes (Tsd/µl) | | | | | | | |
| EPO | 266.95 | 267.95 | 274.89 | 273.90 | 278.95 | 247.05 | 0.004 |
| (N = 19-20) | (73.72) | (64.86) | (91.32) | 72.84) | (76.66) | (62.83) | 0.041 (d.f. = 1, 37)[a] |
| Placebo | 249.58 | 248.74 | 244.26 | 245.37 | 248.21 | 243.89 | |
| (N = 18-19) | (44.14) | (43.40) | (46.17) | (38.35) | (36.75) | (39.92) | |
| Iron (µmol/l) | | | | | | | |
| EPO | 18.37 | 15.69 | 13.60 | 19.28 | 11.73 | 20.86 | 0.007 |
| (N = 19-20) | (12.94) | (11.17) | (9.41) | (12.72) | (7.22) | (6.12) | <0.222 (d.f. = 1, 34)[a] |
| Placebo | 16.49 | 14.26 | 15.09 | 16.28 | 15.53 | 16.63 | |
| (N = 16-19) | (8.21) | (4.88) | (6.82) | (6.82) | (7.68) | (5.89) | |
| Transferria ((µmol/l) | | | | | | | |
| EPO | 35.31 | 34.77 | 35.13 | 35.93 | 36.66 | 32.60 | <0.001 |
| (N = 19-20) | (4.89) | (5.30) | (5.21) | (5.14) | (5.88) | (5.90) | <0.001 (d.f. = 1, 36)[a] |
| Placebo | 27.73 | 29.42 | 29.51 | 29.25 | 30.78 | 30.65 | |
| (N = 18-19) | (3.56) | (6.29) | (6.17) | (6.46) | (5.83) | (4.75) | |
| Transferrin saturation (%) | | | | | | | |
| EPO | 24.56 | 22.17 | 17.48 | 24.77 | 14.43 | 29.54 | <0.001 |
| (N = 19-20) | (20.36) | (21.51) | (11.70) | (18.41) | (8.78) | (9.67) | 0.199 (d.f. = 1, 33)[a] |
| Placebo | 28.12 | 22.48 | 24.35 | 26.15 | 22.54 | 25.35 | |
| N = 16-19 | (16.16) | (7.94) | (13.29) | (12.96) | (12.49) | (9.89) | |

| | Week 1 M (± s.d.) - baseline | Week 2 M (± s.d.) | Week 3 M (± s.d.) | Week 4 M (± s.d.) | Week 5 M (± s.d.) | Week 6 M (± s.d.) | Week 7 M (± s.d.) |
|---|---|---|---|---|---|---|---|
| Ferritin (ng/ml) | | | | | | | |
| EPO | 132.05 | 81.15 | 67.74 | 50.00 | 48.26 | 43.35 | 34.30 |
| (N = 18-20) | (105.66) | (71.44) | (69.30) | (47.57) | (51.57) | (37.54) | (36.36) |
| Placebo | 140.84 | 132.53 | 134.06 | 123.63 | 129.10 | 126.11 | 116.95 |
| (N = 17-19) | (93.43) | (89.88) | (90.44) | (76.44) | (88.16) | (89.11) | (80.92) |
| Erythrocyle sedimentation rate (mm/1 h) | | | | | | | |
| EPO | 10.40 | 6.67 | 6.37 | 9.88 | 6.18 | 6.79 | 4.83 |
| (N = 19-20) | (8.53) | (5.54) | (6.52) | (12.17) | (8.55) | (7.84) | (4.44) |
| Placebo | 7.53 | 10.00 | 8.13 | 8.36 | 9.06 | 9.88 | 12.11 |
| (N = 16-18) | (6.53) | (9.93) | (4.94) | (8.66) | (9.70) | (7.04) | (10.10) |

TABLE 5-continued

Routine laboratory data (N = 15-20, due to missing data; significant differences by f-test are marked in gray)

CRP (mg/l)

| | | | | | | | |
|---|---|---|---|---|---|---|---|
| EPO | 3.68 | 3.62 | 3.14 | 3.89 | 2.94 | 4.59 | 3.21 |
| (N = 19-20) | (1.51) | (2.19) | (1.62) | (1.80) | (0.79) | (5.31) | (1.40) |
| Placebo | 4.83 | 4.48 | 5.45 | 5.53 | 4.01 | 4.76 | 6.25 |
| (N = 17-19) | (4.23) | (2.97) | (4.76) | (5.69) | (2.07) | (3.78) | (7.63) |

Creatinine (mg/dl)

| | | | | | | | |
|---|---|---|---|---|---|---|---|
| EPO | 0.95 | 0.97 | 0.95 | 0.96 | 1.01 | 0.93 | 0.97 |
| (N = 19-20) | (0.14) | (0.15) | (0.16) | (0.16) | (0.21) | (0.14) | (0.18) |
| Placebo | 1.03 | 1.00 | 0.99 | 1.02 | 0.99 | 0.96 | 1.03 |
| (N = 18-19 | (0.17) | (0.16) | (0.12) | (0.15) | (0.15) | (0.15) | (0.19) |

| | Week 6 M (± s.d.) - baseline | Week 9 M (± s.d.) | Week 10 M (± s.d.) | Week 11 M (± s.d.) | Week 12 M (± s.d.) | Week 16 M (± s.d.) | Time (week 1-week 12) Time (week 1-week 12) by group P = value |
|---|---|---|---|---|---|---|---|

Ferritin (ng/ml)

| | | | | | | | |
|---|---|---|---|---|---|---|---|
| EPO | 31.75 | 23.32 | 25.06 | 23.26 | 19.35 | 80.58 | <0.001 |
| (N = 18-20) | (34.14) | (22.54) | (23.02) | (23.73) | (16.32) | (62.68) | <0.001 (d.f. = 1, 36)[a] |
| Placebo | 127.00 | 120.53 | 122.06 | 116.74 | 110.67 | 119.82 | |
| (N = 17-19) | (83.70) | (97.54) | (87.14) | (88.20) | (86.95) | (98.63) | |

Erythrocyle sedimentation rate (mm/1 h)

| | | | | | | | |
|---|---|---|---|---|---|---|---|
| EPO | 7.84 | 7.05 | 5.11 | 5.11 | 8.20 | 5.75 | 0.569 |
| (N = 16-20) | (10.80) | (7.16) | (5.29) | (5.78) | (7.90) | (5.81) | 0.062 (d.f. = 1, 32)[a] |
| Placebo | 13.79 | 8.75 | 9.58 | 10.11 | 9.88 | 7.40 | |
| (N = 15-19) | (14.94) | (8.42) | (7.26) | (9.85) | (9.67) | (5.21) | |

CRP (mg/l)

| | | | | | | | |
|---|---|---|---|---|---|---|---|
| EPO | 2.96 | 3.52 | 4.27 | 3.49 | 3.97 | 3.91 | 0.476 |
| (N = 19-20) | (0.90) | (2.41) | (3.23) | (1.72) | (3.88) | (2.53) | <0.721 (d.f. = 1, 36)[a] |
| Placebo | 5.69 | 4.90 | 6.30 | 5.96 | 5.70 | 5.72 | |
| (N = 17-19) | (8.55) | (3.98) | (7.59) | (5.85) | (5.43) | (7.87) | |

Creatinine (mg/dl)

| | | | | | | | |
|---|---|---|---|---|---|---|---|
| EPO | 0.98 | 0.95 | 0.95 | 0.93 | 0.94 | 0.95 | <0.231 |
| (N = 19-20) | (0.17) | (0.17) | (0.13) | (0.15) | (0.13) | (0.14) | <0.779 (d.f. = 1, 36)[a] |
| Placebo | 1.03 | 0.96 | 1.00 | 0.99 | 1.00 | 0.98 | |
| (N = 18-19) | (0.21) | (0.14) | (0.14) | (0.12) | (0.13) | (0.16) | |

Abbreviations: CRP, C-reactive protein; EPO, erythropoietin; M, mean; MCH, mean corpuscular hemoglobin; MCV, mean corpuscular volume.
[a]Degrees of freedom (d.f.) are identical for time and time by group.

TABLE 6

Additional laboratory data (N = 14-18, due to missing data for these particular assays)

| | Week 1 M (± s.d.) - baseline | Week 2 M (± s.d.) | Week 3 M (± s.d.) | Week 4 M (± s.d.) |
|---|---|---|---|---|

Erythropoietin (mU/ml)

| | | | | |
|---|---|---|---|---|
| EPO (N = 16) | 7.58 (3.18) | 10.06 (4.08) | 8.61 (3.60) | 7.45 (3.03) |
| Placebo (N = 14-15) | 10.20 (4.17) | 9.32 (3.51) | 11.48 (3.46) | 10.49 (5.72) |

Hepcidin (ng/ml)

| | | | | |
|---|---|---|---|---|
| EPO (N = 15) | 322.50 (102.84) | 317.26 (93.43) | — | 324.79 (104.44) |
| Placebo (N = 14-15) | 282.09 (83.50) | 288.65 (137.67) | — | 283.22 (100.43) |

IL-6 (pg/ml)

| | | | | |
|---|---|---|---|---|
| EPO (N = 15) | 1.56 (0.80) | 1.70 (1.27) | — | 1.75 (0.99) |
| Placebo (N = 14-15) | 1.76 (0.91) | 1.82 (0.78) | — | 1.90 (0.99) |

| | Week 5 M (± s.d.) | Week 11 M (± s.d.) | Week 12 M (± s.d.) | Time (week 1-week 12) Time (week 1-week 12) by group, P-value |
|---|---|---|---|---|

Erythropoietin (mU/ml)

| | | | | |
|---|---|---|---|---|
| EPO (N = 16) | 6.86 (3.54) | 7.76 (4.85) | 9.35 (7.84) | 0.355 |
| Placebo (N = 14-15) | 9.90 (4.60) | 11.00 (4.63) | 10.44 (5.72) | 0.479 (d.f. = 1, 29)[a] |

TABLE 6-continued

Additional laboratory data (N = 14-18, due to missing data for these particular assays)

Hepcidin (ng/ml)

| | | | | |
|---|---|---|---|---|
| EPO (N = 15) | — | — | 310.28 (99.86) | 0.870 |
| Placebo (N = 14-15) | — | — | 298.36 (127.53) | 0.254 (d.f. = 1, 28)[a] |

IL-6 (pg/ml)

| | | | | |
|---|---|---|---|---|
| EPO (N = 15) | — | — | 1.72. (1.14) | 0.384 |
| Placebo (N = 14-15) | — | — | 2.02 (1.56) | 0.837 (d.f. = 1, 28)[a] |

Abbreviations: EPO, erythropoietin; IL-6, interleukin-6.
[a]Degrees of freedom (d.f.) are identical for time and time by group.

Figure 10:
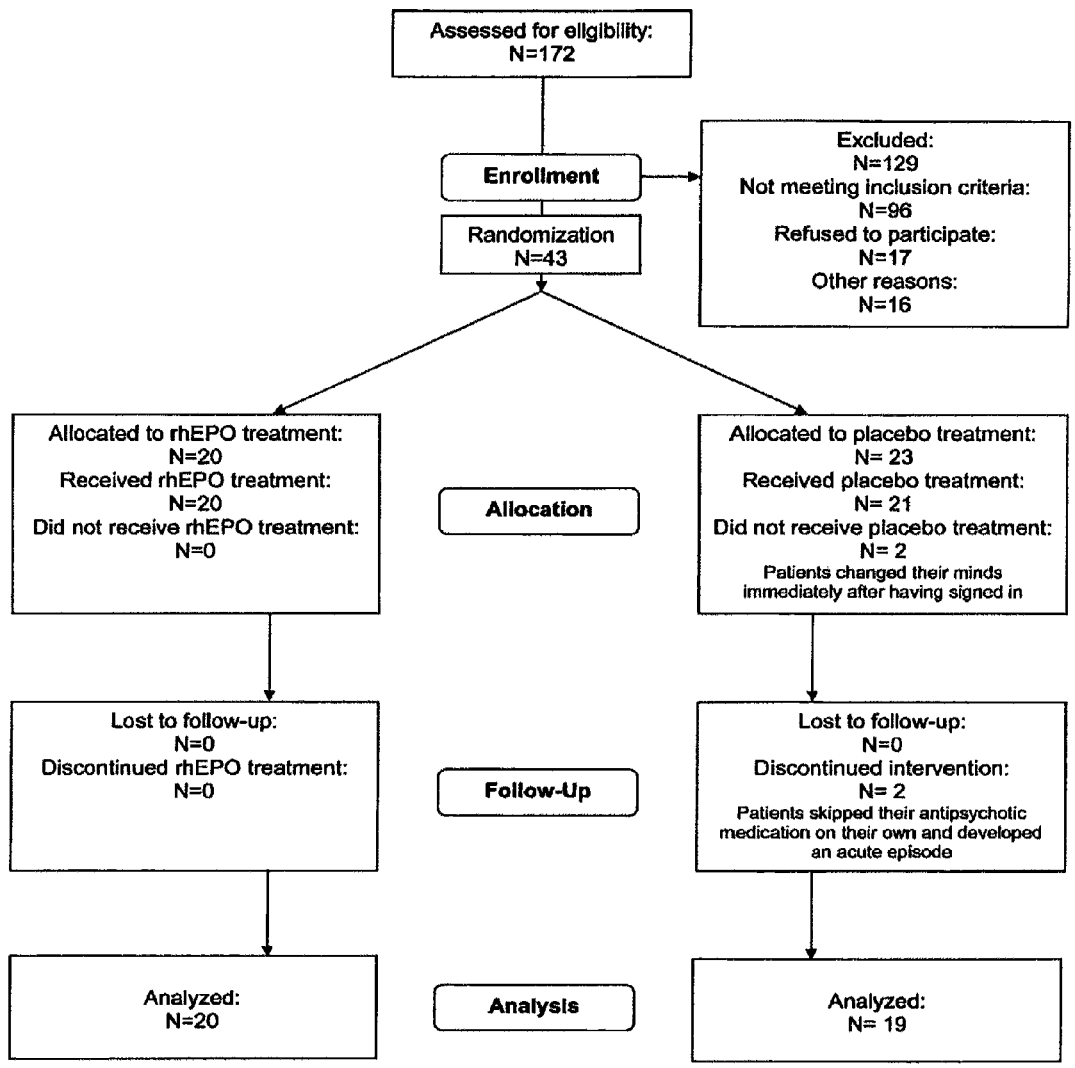
FIG. 10 shows a flowchart of patient recruitment, retention, and follow-up.

FIG. 10 shows a flowchart of patient recruitment, retention, and follow-up

Figure 11:
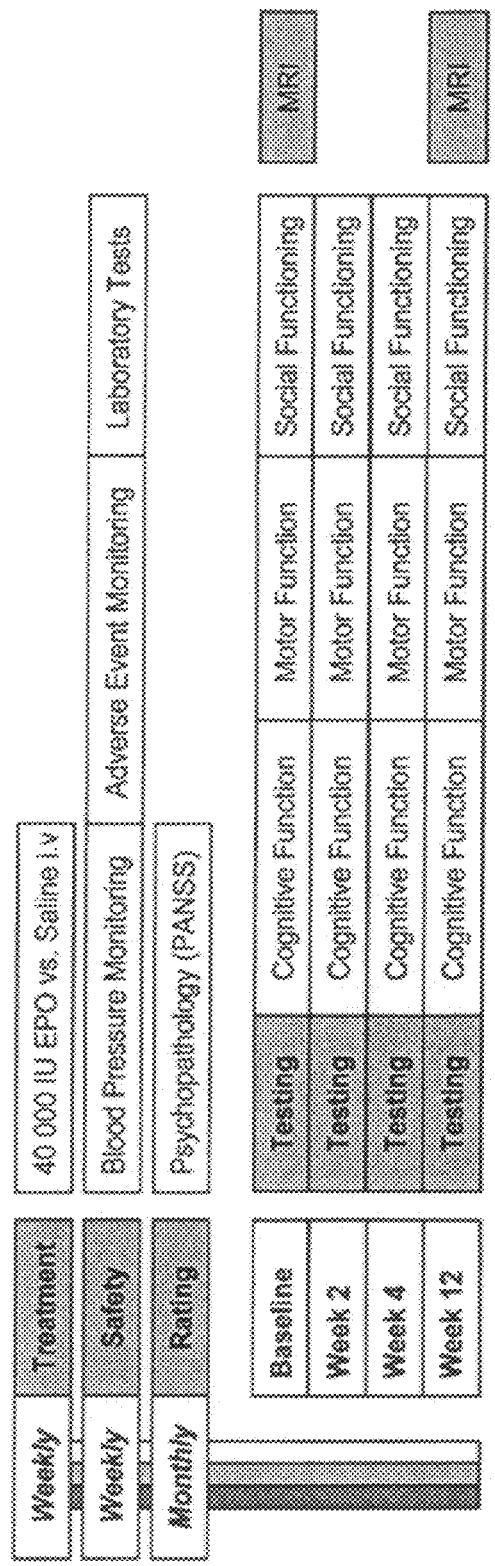
FIG. 11 shows an overview of visits and tests performed during the "EPO chronic schizophrenia add-on trial."

FIG. 11 illustrates an overview of visits and tests performed during the "EPO chronic schizophrenia add-on trial"

FIG. 12 illustrates repeated measures analysis of covariance: Effect of erythropoietin (N=19) versus placebo (N=19) treatment on cognitive parameters in male chronic schizophrenic patients.
Cognitive parameters: Sum score of RBANS subtests Language-Semantic Fluency, Attention, Delayed Memory, plus WCST Perseverative Errors; Covariate: Age;
Strategy: Follow-up of each individual according to his inclusion status.

FIG. 13 illustrates repeated measures analysis of covariance: Effect of erythropoietin (N=15) versus placebo (N=15) treatment on S100B serum levels in male chronic schizophrenic patients. Covariate: Age. As healthy controls, 27 age-matched men, serving as blood donors for the blood bank, were employed.

Materials and Methods
Patients and Procedures

The protocol for the present phase II multicenter trial ("EPO-schizophrenia study") was approved by the ethical committee of the Georg-August-University of Gottingen (master committee) as well as by the respective ethical committees of all other participating centers. Written informed consent by patients or their authorized legal representatives was required. Between April 2003 and March 2005, 39 patients, out of 172 screened for participation, have completed the study (FIG. 1). Of the 43 patients who had originally been included in the study, 2 changed their minds immediately after having signed in, before they received any study medication (both Göttingen), and 2 patients dropped out during the course of the trial (Marburg, Göttingen), both belonging to the placebo group. Both of these late drop-outs skipped their antipsychotic medication on their own, developed an acute episode, and discontinued the trial. All other patients were highly compliant and concluded the study as planned.

The trial was set up as a double-blind, placebo-controlled randomised multicenter trial. Of the 39 study completers, 17 were from Göttingen, 14 from Kiel, 4 from Homburg, 3 from Cologne and 1 from Marburg. Total duration of the study was 2 years (from April 2003 to March 2005), individual duration 12 weeks of weekly treatment with an additional safety visit at 16 weeks. The intervention consisted of weekly administration of rhEPO (40,000 IU of erythropoietin-beta, Roche, Grenzach, Whylen, Germany) or placebo as a short (15 min) intravenous infusion.

After careful baseline examination and confirmation of inclusion/exclusion criteria, patients were asked to return weekly for application of the study drug, documentation of any other medication, monitoring of adverse events and safety, including measurement of blood pressure and routine laboratory testing. Blood letting (350-450 ml) was performed if the hematocrit exceeded 50% on two consecutive weeks.

Study endpoints were cognitive function, tested over 2 days at baseline, and at 2 weeks, 4 weeks, and 12 weeks of study participation. The "cognitive test package" applied included the Repeatable Battery for the Assessment of Neuropsychological Status (RBANS; ABAB design), the Wisconsin Card Sorting Test (WCST-64), and a test of premorbid intelligence (Mehrfachwahl-Wortschatz-Intelligenztest, MWT-B, which was performed only at baseline). Other clinical outcomes were psychopathology measures including Positive and Negative Syndrome Scale (PANSS) at baseline, 2 weeks, 4 weeks, 8 weeks and 12 weeks. Further instruments included the Subjective Well-Being under Neuroleptic Treatment (SWN), the Disability Assessment Schedule (DAS-M), both performed at baseline, 2 weeks, 4 weeks and 12 weeks. As motor tests, the subtests Tapping and Dotting from the MacQuarrie Test for Mechanical Ability were performed at baseline, 2 weeks, 4 weeks and 12 weeks.

For morphological assessment, magnetic resonance imaging (MRI) was conducted at baseline and after 3 months. High-resolution 3D T1-weighted gradient echo sequences (spoiled 3D FLASH, 1 mm isotropic) were applied. Volumetrical analysis was performed using FSL 3.2 Software (FMRIB Analysis Group, Oxford). Datasets of baseline and follow up examinations were co-registered and analysed using the SIENA tool (Structural Image Evaluation Using Normalisation of Atrophy) of FSL. For basic primary analysis, whole brain volume was assessed.

In order to provide optimal logistics, e.g. with respect to timely delivery of study medication to the centers, and to guarantee the highest possible interrater agreement, a comprehensive 2-day training workshop was organized for all participating centers and their physicians/psychologists. FIG. 2 gives an overview of visits and tests performed during the trial.

Inclusion and Exclusion Criteria

For homogeneity reasons, only male patients were included, age 25-50 years. They had to meet criteria for DSM IV diagnosis of schizophrenia. At least 10 years should have elapsed since hospitalization due to their first acute episode. Patients should not have had any acute episode throughout the previous six months, negative symptoms had to have stably existed throughout the previous year. On presentation for study participation, PANSS Negative Syndrome Scale was required to be ≧20, PANSS General Psychopathology Scale ≧48. Only patients with outlasting cognitive deficits affecting working memory, executive functions, and attention were included. Their cognitive performance had to be at least one standard deviation below normal in the RBANS.

Exclusion criteria were acute psychosis as characterized by a change in state, requiring an intervention (additionally, requirement of a PANSS Positive Syndrome Scale ≧28 should restrict severity of positive symptoms in the patient population), organic psychosis, other severe diseases, use of illicit drugs, alcohol dependence, high thrombembolic risk factors, myeloproliferative disorders or hematocrit >50%. Study-related exclusion criteria would have been (1) interruption of study medication for more than two weeks or (2) missing of study medication more than two times (20%). Safety-related exclusion criteria would have been a diastolic blood pressure ≧100 mm Hg twice daily on three consecutive days.

All medication had to be documented. Prerequisite for inclusion was stable medication with psychoactive drugs at least over the last 2-3 months. Regarding antipsychotic treatment, both typical and atypical antipsychotics were allowed. Patients with stable benzodiazepine medication were not excluded. Additional psychotropic medication, including newly prescribed benzodiazepines, had to be avoided. For critical situations, requiring short term additional medication (2 cases), neuropsychological testing had to be postponed until at least 8 days after the last administration of this medication (e.g. benzodiazepines).

For blinding, the pharmacist prepared and numbered identical vials containing either saline (0.9% NaCl) or rhEPO reconstituted in saline. Upon enrolment, the vials were randomly assigned to patients with the contents of vials known only by the pharmacist. For randomization, a block design with approximately equal numbers of subjects randomized to each condition according to site was applied. To guarantee double-blinding as much as possible, none of the clinicians performing neuropsychological or psychopathological analysis had access to any of the laboratory data obtained (red blood cell counts, including reticulocytes, parameters of iron metabolism) during the study. Serum-EPO levels were analyzed only after unblinding of the study.

Assays for EPO, S100B, interleukin-6 and hepcidin prohormone in serum Concentrations of EPO were measured in serum, using a commercially available ELISA kit (R&D Systems, Wiesbaden, Germany) according to the manufacturer's protocol. Commercial assays were also used for determining S100B (DiaSorin, Dietzenbach, Germany), interleukin-6 (IL-6, R&D Systems, Wiesbaden, Germany), and hepcidin prohormone (DRG Instruments GmbH, Marburg, Germany). Serum samples were not analyzed before unblinding of the study. Sample analysis of EPO and placebo patients was performed blinded and in random order, using adequate inter- and intraassay controls. Inter- and intraassay coefficients of variation did not exceed 8% in any of the assays.

Routine Laboratory Analyses

Determination of routine laboratory data was performed in the Department of Clinical Chemistry of the Georg-August-University Goettingen, according to standard procedures.

Statistical Analysis

Primary outcome measure in this proof-of-principle study was a neuropsychological test set covering functions that were (1) found to be most severely impaired in our patient population at baseline and (2) known to be predominantly affected in chronic schizophrenia: RBANS subtests delayed memory, language-semantic fluency, and attention, as well as Wisconsin Card Sorting-perseverative errors. For analysis, raw data were used throughout the paper. To determine the composite score, they were z-transformed. For illustration of the core findings in FIG. 12, z-transformation was followed by IQ-transformation, and expression of the data as % individual baseline. The exploratory use of normative instead of raw data yielded comparable results and significance levels.

Although the present trial—including our cognitive test set—has been designed well before the NIMH initiative on Measurement and Treatment Research to Improve Cognition in Schizophrenia (MATRICS), the test set covers 6 of the 7 domains of the MATRICS consensus cognitive battery for use in clinical trials: Speed of processing, attention/vigilance, working memory, verbal learning and memory, visual learning and memory, reasoning and problem solving. Only the MATRICS domain "social cognition" is not specifically contained in our test set. Among the cognitive tests performed but not included in the test set, mainly due to their lower sensitivity in schizophrenic patients, were RBANS subtests visuospatial function, language-picture naming, and immediate memory. Secondary endpoints were time dependent changes in psychopathology scores, motor function (tapping and dotting), blood parameters, and MRI volumetrical data.

Several considerations guided the approach to the data analysis. First, repeated measures analysis of covariance (repeated measures ANCOVA) was performed, with the primary outcome measure (schizophrenia-related cognitive test set) serving as the dependent variable, and treatment as the independent variable, and with age (a major determinant of neuropsychological functioning) as a covariate in the analysis. Addition of other covariates such as MWT-B (a measure of pre-morbid intelligence) or type and amount of medication did not change the results of the analysis (see Results). In order to account for the tendency of different baseline performance in cognitive testing found upon unblinding of the study between the two groups, the same analysis as described above was performed with the exception that cognitive outcome measures were expressed as percent of the individual baseline level. This way of analysis further confirmed the results (see Results section). Additional statistical testing included t-tests, chi$^2$-tests, and Pearson correlations. For all statistical analyses, the program SPSS for Windows, release 12, was used. All tests were two-tailed and, due to the exploratory character of the study, p-values were not adjusted for the number of tests that were performed. Thus, results should be considered of being preliminary. Mean (M) and standard deviation (SD) are given to describe results in the text and tables, whereas in the figures mean (M) and standard error of the mean (SEM) are used.

In the present study we show that a neuroprotective/neurotrophic add-on strategy in a group of chronically ill schizophrenic men with defined cognitive deficit can lead to improvement of cognition. Weekly intravenous application of high dose rhEPO over 12 weeks apparently induced a stepwise amelioration in a set of cognitive functions known to be most severely affected in schizophrenia. Additionally, EPO treatment resulted in a significant decrease in serum levels of the glial damage marker S100B. In contrast, rhEPO add-on treatment was unable to affect psychopathology ratings, measures of social functioning, or brain volume during the 3 months of observation. In fact, all patients, placebo as well as EPO treated, improved during the study with respect to negative symptoms and general psychopathology.

Interestingly, the placebo group also showed cognitive improvement over the whole study period. This study-related, EPO-independent, effect on cognition goes hand in hand with the EPO-independent effects on negative symptoms and general psychopathology, and may to some degree be explained by the positive change in the monotonous life of these chronically ill patients through additional regular therapeutic and caring social interactions. Common factors like social training and increased structure, motivation and expectancy, recognition and importance, boosting self-confidence, may play a role. Despite using an ABAB design of the two versions of the RBANS, a battery characterized by repeatability, a neuropsychological training effect adding to the observed improvement in the placebo group cannot be entirely ruled out. In any case, the EPO group by far exceeds the placebo group with respect to cognitive outcome.

EPO was able to clearly and gradually improve cognition without affecting any of the other schizophrenia typical symptoms. This distinct separation of effects by the drug might (1) point against a secondary beneficial effect on cognitive performance, e.g. via reduction of negative symptoms and (2) allow for further conclusions with respect to disease-specific pathophysiological mechanisms.

Despite some recent literature describing beneficial effects of various antipsychotics on cognitive functioning, none of these studies has provided convincing evidence of cognitive improvement unrelated to recovery from acute episodes of the disease. Also, in these studies, different antipsychotics have been tested against each other. In contrast, EPO has been able as an add-on treatment, on top of a stable antipsychotic medication regime, to specifically target cognition in a group of chronic schizophrenic patients with clearly defined, persistent cognitive decline. Even though the principal question may arise of what the clinical significance of an improvement in cognition over baseline of 16% and over placebo of 7% might be, we strongly feel that the main issue of the present proof-of-concept study is to show that the concept works. Also, from the observed course of improvement, there might still be capacity for further improvement with continued treatment.

We interpret the effect of EPO to be of regenerative nature rather than to be due to a temporary cognitive enhancement, for two reasons: (1) The steady increase in cognitive performance over time; (2) The fact that EPO serum levels returned back to normal each week before the next application of EPO. The gradual improvement in cognition therefore occurred in the absence of an accumulation of compound.

Regarding the mechanism of action of EPO on cognition in schizophrenia, the gradual pattern of improvement may point to a morphological rather than a purely functional and short-lived effect. Not surprising, however, we have not been able to detect any changes in whole brain volume as early as after 3 months of EPO treatment since measurable results on brain dimensions might not occur before 6 months. Nevertheless, it was of importance, in light of planning future studies, to perform MRI before and after this first neuroprotective proof-of-concept trial in schizophrenia. Interestingly, EPO has been shown to influence synaptic/dendritic density and function (synaptic transmission). Thinking along these lines, improvement in cognition and in learning processes has been closely related to activation of MAP kinases. These second messengers, in turn, are known to be stimulated by EPO in neurons.

Another novel finding was the effect of EPO treatment on serum levels of the glial damage marker, S100B. Both groups, EPO and placebo, started out from identical baseline levels, not different from healthy controls. Although our healthy control levels are comparable to those reported by others, the finding of normal values in schizophrenic patients is in some contrast to reports on elevated serum concentrations in this condition. In most previous publications, however, only patients within or shortly after an acute episode were investigated, whereas our inclusion criteria required the last episode dating back to more than 6 months. Surprisingly, despite normal S100B baseline levels, schizophrenic patients respond to rhEPO with a further decrease. Assuming that S100B is brain-derived, this phenomenon may have essentially two explanations: (1) EPO "seals" the blood brain-barrier and prevents S100B from crossing into the circulation; (2) EPO reduces intracerebral S100B production. While there is evidence of an effect of EPO on blood-brain-barrier function, an interference of EPO with S100B production/release has not been reported yet (in a series of preliminary experiments, we did not find any evidence of a suppressive effect of EPO on S100B release from human astrocytoma (U373) cells or an effect of EPO on cellular S100B content (data not shown). In line with either one of these two interpretations, however, rhEPO was able to reduce elevated S100B levels in our previous stroke trial. Nevertheless, it cannot be entirely excluded at this point that S100B in our schizophrenic patients is derived from other S100B producing tissues, e.g. muscle or gut, and that EPO interferes with their production, release, or elimination of S100B. Interestingly, mutant mice, devoid of S100B, show improved memory function and enhanced longterm potentiation in hippocampal slices.

EPO was found to be safe in our hands in this particular setting. Patients were followed closely from week to week, and blood lettings were performed wherever necessary and were well tolerated. No adverse events, in particular no thrombembolic complications or effects on blood pressure, were reported or observed. Nevertheless, recently developed non-erythropoietic EPO analogues like carbamylated EPO (CEPO) might be the compounds of choice to exploit neuroprotective effects of EPO without having to deal with its hematopoietic properties.

Despite the fact that both the group of patients and the effect on cognition were rather small, we hope that the present work will encourage new treatment strategies in schizophrenia. In this regard, our study has stimulated a number of additional questions and challenges: We cannot be sure whether dose and frequency of rhEPO application is already optimized. Moreover, future studies should also extend to first episode or even prodromal patient groups. They will have to last longer than 12 weeks and should include regular cognitive training, physical exercise and enhanced social exposure. We hypothesize that EPO will be most beneficial in a situation of major functional challenge. Rather than treating healthy sportsmen to ever increasing performance without any good reason, EPO should be explored and exploited for "brain doping" in ill patients where it may have profound and lasting beneficial effects.

In a test series on three schizophrenics in the subacute illness stage (first or second manifestation) and on two healthy patients, there was administered intravenously on one occasion to the individual patients respectively 40,000 IU indium-111-erythropoietin with in total 120-185 MBq. Subsequently, single photon emission computer tomographies (SPECT-pictures) were taken, the pictures being produced 4.18 to 21 or 42 to 45 hours after administration of the radioactively marked erythropoietin.

The subsequent Table 1 shows the quotients "average impulse content of the brain/average impulse content of the bone marrow of the skull cap".

|  | 4 h | 18-21 h | 42-45 h |
| --- | --- | --- | --- |
| Experimentee 1 | 0.69 | 0.49 | 0.46 |
| Experimentee 2 | 0.61 | 0.47 | 0.43 |
| Patient 1 | 0.75 | 0.59 | 0.58 |
| Patient 2 | 0.80 | 0.56 | 0.50 |
| Patient 3 | 0.76 | 0.64 | 0.49 |

In the three patients 1 to 3 with schizophrenia, a clear intracerebral accumulation of the radioactively marked erythropoietin is shown at all three points in time, this accumulation being globally higher in the patients 1 to 3 than in the healthy experimentees 1 and 2. This multiaccumulation of the radioactive erythropoietin can be seen immediately from the quotients shown in Table 1.

It has been shown for the first time hence that erythropoietin surmounts the blood-brain barrier more strongly in the case of schizophrenics in the (sub)acute phase of the psychosis than in the case of healthy people. Furthermore, it has been established for the first time that erythropoietin is able to surmount this even in the case of healthy people with an intact blood-brain barrier with a correspondingly high dosage. Hence a chronic treatment of schizophrenics, even beyond the acute illness phase, i.e. even in the case of a blood-brain barrier which is intact again, can effect sufficiently high intracerebral levels as neuroprotective add-on therapy.

Erythropoietin is thereby able to influence all three mechanisms potentially involved in the pathogenesis of the schizophrenia, said mechanisms resulting in a neuronal dysfunction:

a) apoptosis;
b) metabolic disorder of the nerve cells;
c) synaptic junctions/axon sprouting.

The precondition for the neuroprotective effect of erythropoietin in the brain of schizophrenics, which is sought after here, is its bonding to specific erythropoietin receptors on nerve cells. These were detected for the first time in the immune-histochemical studies carried out for the present invention.

Because increasing or prolonging the activation and/or stimulation of the erythropoietin receptors in the brain of the schizophrenics is important to the treatment and prevention of schizophrenia and its related psychoses as shown in the invention, the scope of the invention should expand to include any known substance that increases or prolongs the activation and/or stimulation of the EPO receptor, or acts as a agonist to said receptor in any way.

FIG. 1 shows a histological section from the hippocampus of a schizophrenic (post mortem brain) in which, by means of immune-histochemistry, erythropoietin receptors (EPOR: red coloration, left image, FIG. 1A) and by means of a double fluorescence method, the localization of the same could be detected on nerve cells (EPOR: orange coloration, NeuN=nerve cell marker; green coloration, right image, FIG. 1B). It can be detected immediately that the green fluorescent nerve cells are also marked with red fluorescent EPOR antibodies so that an orange coloration is produced in FIG. 1B. It has been established for the first time with this study that nerve cells in the brain of schizophrenics have immunoreactivity for erythropoietin receptors.

Therefore, increasing or prolonging the activation and/or stimulation of the erythropoietin receptors by any known substance to be capable of such activity is not beyond the scope of this invention.

For FIGS. 1A and 1B, the sections were deparaffinated in Hemo-DE (Fischer Scientific, Schwerte, Germany), three washing steps were implemented for 5 minutes, they were rehydrated in a decreasing alcohol sequence, washed with distilled water, boiled in citrate buffer, washed in tris buffered common salt solution (TBS), incubated with 10% blocking serum in 0.05% Tween-20/TBS at room temperature and subsequently incubated with a polyclonal hare-anti-human EPOR antibody (1:200, C-20, Santa Cruz Biotechnology, Heidelberg, Germany) in 2% goat serum/PBS at 4° C. overnight. After washing in 0.05% Tween-20/TBS, the sections were incubated with Texas Red-marked goat-anti-hare antibodies (1:100, Vector Laboratories Inc., Burlingame, Calif., USA) in a humidity chamber (30 min). After washing with 0.05% Tween-20/TBS, the sections were incubated with a monoclonal mouse-antineuronal core (NeuN)antibody (1:500, Chemcon Int. Inc., Temecula, Calif., USA) in 2% horse serum/PBS at +4° C. (24 h), washed in 0.05% Tween-20/TBS and incubated in a humidity chamber with horse-anti-mouse antibodies marked with fluoresceine (FITC) (1:100, vector) for 30 min. The sections were then washed in 0.05% Tween-20/TBS and TBS and finally embedded in Vectashield (vector) fluorescence medium.

What is claimed is:

1. A method for treatment of acute schizophrenia in a human being with acute schizophrenia, comprising the step of administering an effective dose of recombinant erythropoietin as an add-on therapy to the human being.

2. The method according to claim 1, comprising the step of vascularly administering recombinant erythropoietin as an add-on therapy.

3. The method according to claim 1, comprising the step of intravenously administering recombinant erythropoietin as an add-on therapy.

4. The method according to claim 1 wherein recombinant erythropoietin as an add-on therapy is administered in a dose of 5,000 IU to 200,000 IU per administration or per day or per week.

5. The method according to claim 1 wherein recombinant erythropoietin as an add-on therapy is administered in a dose of 35,000 IU per administration or day.

6. The method according to claim 1 wherein recombinant erythropoietin as an add-on therapy is administered in a dose of 5,000 IU to 35,000 IU per administration or per day or per week.

7. The method according to claim 1, wherein the human being is concurrently administered anti-psychotic medication.

8. The method according to claim 1, wherein the human being is concurrently administered a symptom-arresting neuroleptic.

* * * * *